(12) United States Patent
Okumura et al.

(10) Patent No.: US 12,414,749 B2
(45) Date of Patent: Sep. 16, 2025

(54) X-RAY DIAGNOSIS APPARATUS AND CONTROL METHOD OF THE SAME

(71) Applicant: CANON MEDICAL SYSTEMS CORPORATION, Otawara (JP)

(72) Inventors: Yusuke Okumura, Nasushiobara (JP); Haruki Iwai, Otawara (JP); Motohiro Sato, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 272 days.

(21) Appl. No.: 18/181,695

(22) Filed: Mar. 10, 2023

(65) Prior Publication Data
US 2023/0284992 A1  Sep. 14, 2023

(30) Foreign Application Priority Data

Mar. 14, 2022  (JP) ................. 2022-039600

(51) Int. Cl.
  *A61B 6/40* (2024.01)
  *A61B 6/00* (2006.01)
  *A61B 6/46* (2024.01)
  *G06T 1/60* (2006.01)
  *G06T 5/50* (2006.01)
  *G06T 7/20* (2017.01)

(52) U.S. Cl.
  CPC .............. *A61B 6/487* (2013.01); *A61B 6/463* (2013.01); *A61B 6/465* (2013.01); *A61B 6/467* (2013.01); *A61B 6/5235* (2013.01); *A61B 6/5264* (2013.01); *A61B 6/54* (2013.01); *G06T 1/60* (2013.01); *G06T 5/50* (2013.01); *G06T 7/20* (2013.01); *G06T 2200/24* (2013.01); *G06T 2207/10121* (2013.01); *G06T 2207/20081* (2013.01); *G06T 2207/20212* (2013.01); *G06T 2207/30004* (2013.01); *G06T 2207/30168* (2013.01)

(58) Field of Classification Search
CPC .......... A61B 6/487; A61B 6/463; A61B 6/465
See application file for complete search history.

(56) References Cited

U.S. PATENT DOCUMENTS

| | | | |
|---|---|---|---|
| 9,280,837 B2 | 3/2016 | Grass et al. | |
| 2003/0169847 A1* | 9/2003 | Karellas | A61B 6/504 378/98.3 |
| 2004/0122790 A1* | 6/2004 | Walker | A61B 5/318 |
| 2011/0182492 A1 | 7/2011 | Grass et al. | |

(Continued)

FOREIGN PATENT DOCUMENTS

| | | |
|---|---|---|
| JP | 10-234714 A | 9/1998 |
| JP | 2009-183509 A | 8/2009 |
| JP | 2012-505009 A | 3/2012 |

*Primary Examiner* — Hugh Maupin
(74) *Attorney, Agent, or Firm* — Oblon, McClelland, Maier & Neustadt, L.L.P.

(57) ABSTRACT

An X-ray diagnosis apparatus according to the present embodiment comprises: an imager configured to image by irradiating X-ray to a subject to acquire a captured image by X-ray imaging and a fluoroscopic image by fluoroscope imaging; and processing circuitry configured to acquire imaging related information obtained within a certain period of time before or after the X-ray imaging, and store in a memory the fluoroscopic image captured at least one of before or after the X-ray imaging based on the imaging related information.

13 Claims, 24 Drawing Sheets

(56) References Cited

U.S. PATENT DOCUMENTS

| | | | | |
|---|---|---|---|---|
| 2020/0121294 A1* | 4/2020 | Tsymbalenko | ....... | A61B 8/5246 |
| 2020/0222018 A1* | 7/2020 | van Walsum | ........ | A61B 6/5264 |
| 2021/0404974 A1* | 12/2021 | Nagatsuka | ............. | A61B 6/465 |
| 2022/0395251 A1* | 12/2022 | Tsymbalenko | ........... | G06N 3/08 |

* cited by examiner

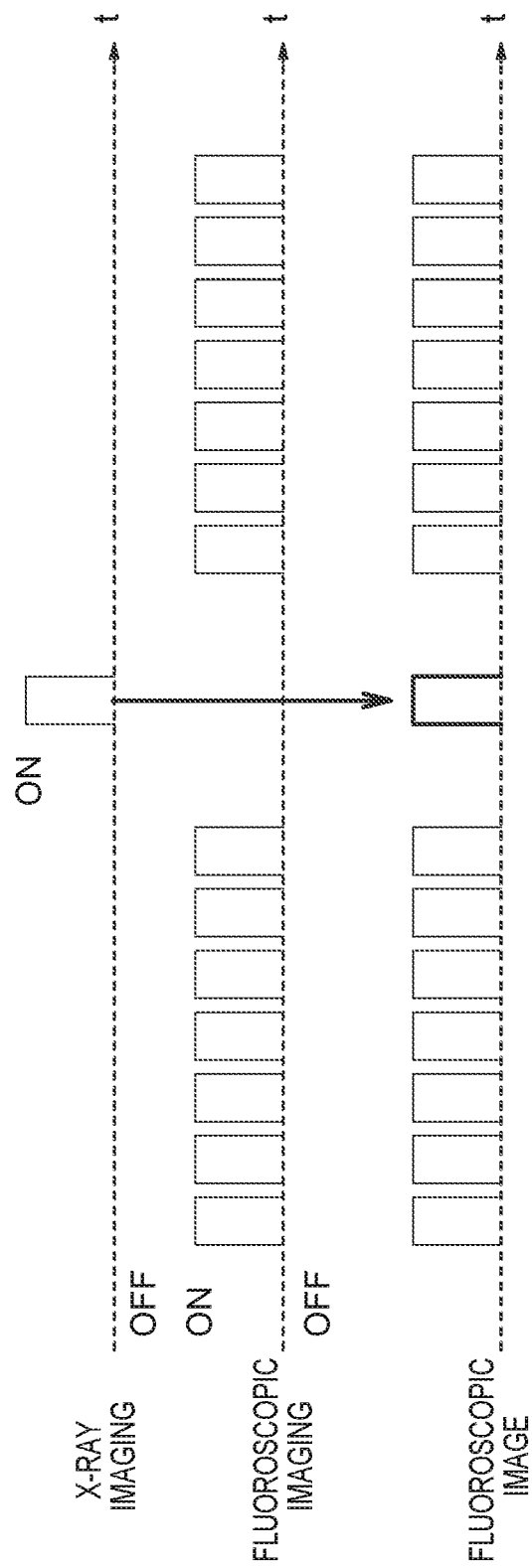

X-RAY DIAGNOSIS APPARATUS AND CONTROL METHOD OF THE SAME

CROSS-REFERENCE TO RELATED APPLICATIONS

This application is based upon and claims the benefit of priority from the prior Japanese Patent Application No. 2022-039600, filed on Mar. 14, 2022, the entire contents of which are incorporated herein by reference.

FIELD

The embodiments disclosed in the present specification and drawings relate to an X-ray diagnosis apparatus and a control method of the same.

BACKGROUND OF THE INVENTION

Conventionally, in medical fields, X-ray TV bed apparatuses that acquire captured image (single shot of X-ray image) or fluoroscopic image (X-ray images that are continuous in time) by irradiating X-ray to a subject and detecting the X-ray that has passed the subject, are well known. When acquiring the captured image using the X-ray TV bed apparatus, the user must acquire the fluoroscopic image by the fluoroscopic imaging that irradiates X-ray continuously and determine the X-ray imaging location with respect to the subject or the X-ray imaging region etc., while observing the acquired fluoroscopic image.

Typically, the user diagnosis lesions etc. by observing captured images acquired by X-ray imaging. However, if there are blurs of a contrast agent in the captured image, there may be difficulties for the user in diagnosing the lesions etc., using the captured image with the blurs of the contrast agent. For this reason, the user must diagnose the lesions etc., observing the fluoroscopic image that are fluoroscopically imaged before or after the X-ray imaging if blurs of the contrast agent occur. That is, since fluoroscopic imaging, with the captured image, is an effective diagnostic material to the user, there is a need to store the fluoroscopic image with the captured image in the memory for the X-ray TV bed apparatuses.

However, since fluoroscopic image consists of X-ray images that are continuous in time, i.e., a plurality of X-ray images, storing all fluoroscopic image that are fluoroscopically imaged in the memory will oppress the memory capacity. Thus, the user must store only the necessary fluoroscopic image in the memory; however, performing additional operations other than the imaging operation to store the fluoroscopic image in the memory is troublesome for the user, and there arises a problem that the user forgets the additional operations other than the imaging operation. Likewise, this problem similarly arises not only for X-ray TV bed apparatus but also for other X-ray diagnosis apparatus such as an X-ray Angio apparatus; thus, it is desired to store the fluoroscopic image in an appropriate and a simple manner.

BRIEF DESCRIPTION OF DRAWINGS

FIG. 24 is a timing chart that illustrates a timing of inserting an interpolated image, executed in the X-ray diagnosis apparatus according to the sixth modification.

DETAILED DESCRIPTION OF THE INVENTION

With reference to the drawings below, embodiments of an X-ray diagnosis apparatus and a control method of the same will be described. Note that, in the description below, same reference signs are given for components substantially identical in terms of configuration and function, and duplicate description will be given only when necessary.

First Embodiment

Figure 1:
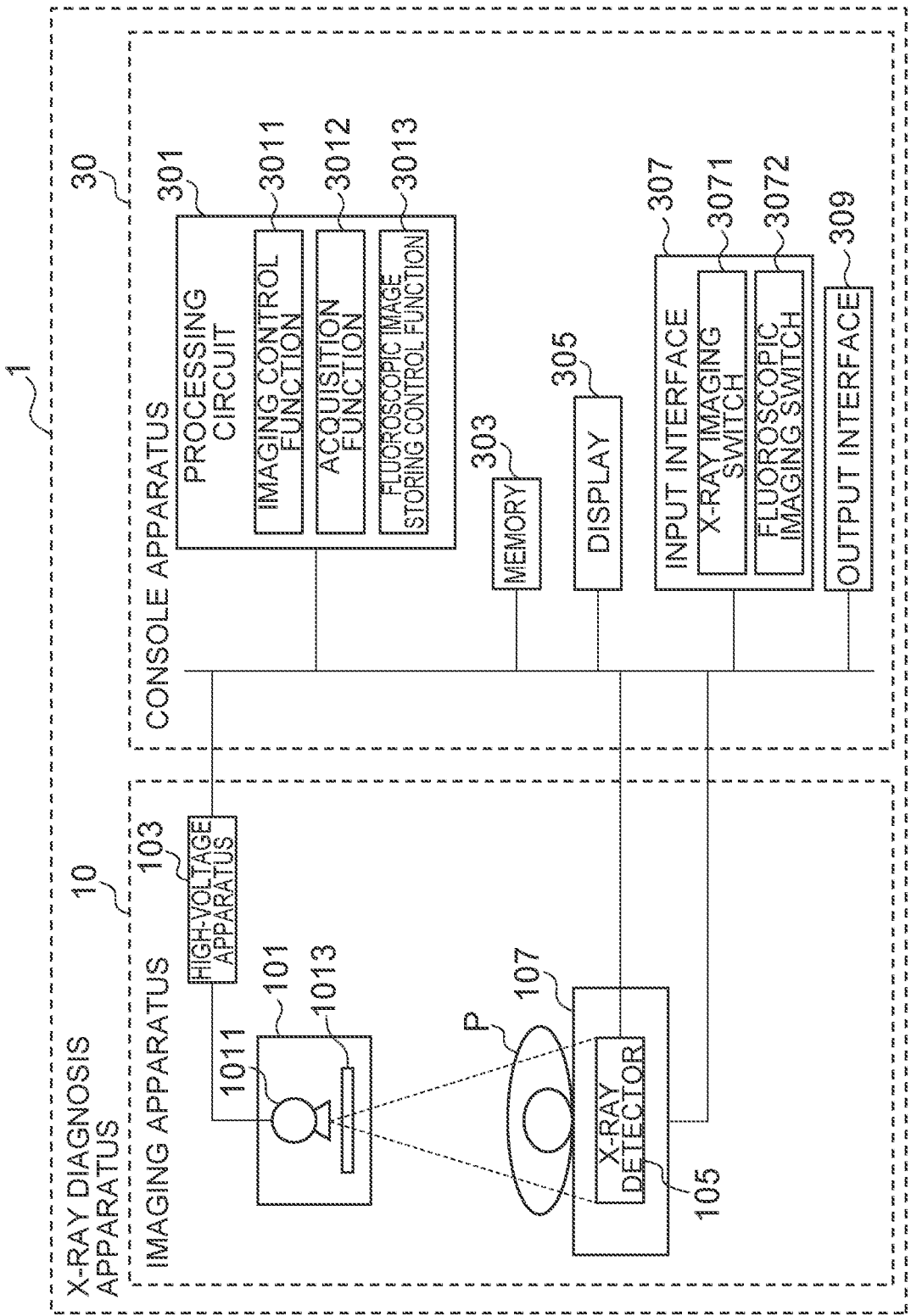
FIG. 1 is a block diagram that illustrates an exemplary configuration of an X-ray diagnosis apparatus according to a first embodiment.

FIG. 1 is a block diagram that illustrates an exemplary configuration of an X-ray diagnosis apparatus according to a first embodiment. The X-ray diagnosis apparatus 1 shown in FIG. 1, for instance, is an X-ray TV bed apparatus. Note that, the X-ray diagnosis apparatus 1 according to the present embodiment is not limited to the X-ray TV bed apparatus, but for instance, may be realized by an X-ray Angio apparatus or a general X-ray imaging apparatus. In the description below, an example where the X-ray diagnosis apparatus 1 is the X-ray TV bed apparatus will be described.

As shown in FIG. 1, the X-ray diagnosis apparatus 1 according to the present embodiment comprises an imaging apparatus 10 and a console apparatus 30.

The imaging apparatus 10 irradiates X-ray to a subject P, and acquires a captured image by X-ray imaging and a fluoroscopic image by fluoroscopic imaging. Note that the imaging apparatus 10 is an example of an imager.

X-ray imaging is an imaging that acquires a single X-ray image as a captured image by discontinuously irradiating X-ray to a subject P. That is, X-ray irradiation is used when acquiring a single captured image by irradiating X-ray once to subject P at a relatively high tube voltage. Note that, X-ray imaging is not limited to be used when acquiring the single captured image, but may be used to acquire X-ray images that are continuous in time by continuously irradiating X-ray to subject P at the relative high tube voltage, i.e., for video capturing. X-ray imaging may acquire X-ray images that have higher resolutions compared to that of fluoroscopic imaging.

Fluoroscopic imaging is an imaging that acquires X-ray images as a fluoroscopic image that are continuous in time by continuously or intermittently irradiating X-ray to subject P. That is, fluoroscopic imaging is used when acquiring a plurality of fluoroscopic image that are continuous in time at a preset framerate by continuously or intermittently irradiating X-ray to subject P at the relatively low voltage. fluoroscopic imaging may be used for video capturing. fluoroscopic imaging may suppress exposure dose to the subject P compared to when performing video capturing by X-ray imaging. Likewise, since fluoroscopic imaging continuously irradiates X-ray to the subject P at a relatively low voltage compared to when performing video capturing with X-ray imaging, a data amount of video capturing per unit time may also be suppressed. The fluoroscopic imaging is broadly classified into continuous fluoroscopic imaging and pulse fluoroscopic imaging. Continuous fluoroscopic imaging is the fluoroscopic imaging where X-ray is continuously irradiated, and pulse fluoroscopic imaging is the fluoroscopic imaging where X-ray pulses are repeatedly irradiated. The pulse fluoroscopic imaging is inferior in the framerate of the fluoroscopic image but may suppress the exposure dose to the subject compared to the continuous fluoroscopic imaging. Note that, hereinafter, continuous fluoroscopic imaging and pulse fluoroscopic imaging will be simply referred to as fluoroscopic imaging when referring to without classification. Likewise, fluoroscopic imaging may acquire the single fluoroscopic image by irradiating X-ray once to the subject P.

The imaging apparatus 10 also comprises an X-ray irradiating module 101, a high voltage apparatus 103, an X-ray detector 105, and a bed 107.

The X-ray irradiating module 101 irradiates X-ray to the subject P. Specifically, the X-ray irradiating module 101 comprises an X-ray tube 1011 that generates X-ray and an X-ray apparatus 1013 that limits an X-ray irradiation field or weakens X-ray for a portion of the irradiation field.

The X-ray tube 1011 is a vacuum tube that has a cathode (filament) that generates thermal electrons and an anode (target) that generates X-ray by receiving thermal electron collisions. The X-ray tube 1011 generates X-ray by using high voltage supplied from the high voltage apparatus 103 to irradiate thermal electrons from the cathode towards the anode. For instance, the X-ray tube 1011 may be a rotary anode type X-ray tube that generates X-ray by irradiating thermal electrons to a rotating anode.

The X-ray aperture 1013 is configured by metal plates such as a lead plate. The X-ray aperture 1013 narrows the X-ray generated by the X-ray tube 1011 to control the range of X-ray irradiation to subject P. That is, the X-ray irradiation range may be narrowed by closing the aperture of the X-ray aperture 1013, or in contrast, widen the X-ray irradiation range by opening the aperture of the X-ray aperture 1013. Note that the X-ray aperture 1013 may be called as a collimator.

The high voltage apparatus 103 supplies high voltage to the X-ray tube 1011 of the X-ray irradiating module 101 under the control of a processing circuit of the console apparatus 30. For instance, the high voltage apparatus 103 has electric circuits such as a transformer and a rectifier, a high voltage generating apparatus that generates high voltage to apply to the X-ray tube 1011, and an X-ray control apparatus that performs control of an output voltage in response to the X-ray irradiated by the X-ray tube 1011. Note that the high voltage generating apparatus may be the transformer type of an inverter type.

The X-ray detector 105 may be a flat panel detector (FPD) that has detection elements arranged in a matrix shape. The X-ray detector 105 detects X-ray irradiated from the X-ray irradiating module 101 which passed through the subject P and outputs the detection signal in response to the detected amount of X-ray to the processing circuit of the console apparatus 30. Note that the X-ray detector 105 may be an indirect conversion type detector that has a grid, scintillator array or an optical sensor array, or a direct conversion type detector that has semiconductor elements that convert incident X-ray to electrical signals.

A bed 107 is a bed that accepts the subject P. X-ray imaging and/or fluoroscopic imaging are performed by the subject P lying on a top board of the bed 107. Thus, the X-ray detector 105 is located below the bed 107.

The console apparatus 30 comprises the processing circuit 301, a memory 303, a display 305, an input interface 307, and an output interface 309.

The processing circuit 301 is a control circuit that performs an overall control of the X-ray diagnosis apparatus 1 and also an arithmetic circuit that performs various operations. For instance, the processing circuitry 301 according to the present embodiment has an imaging control function 3011, an acquisition function 3012, and a fluoroscopic image storing control function 3013. The imaging control function 3011 is equivalent to an imaging control unit according to the present embodiment, the acquisition function 3012 is equivalent to an acquiring unit according to the present embodiment, and the fluoroscopic image storing control function 3013 is equivalent to a fluoroscopic image storing control unit according to the present embodiment.

In the embodiment of FIG. 1, each processing functions performed the imaging control function 3011, the acquisition function 3012, and the fluoroscopic image storing control function 3013 are stored in the memory 303 in a form of computer executable program. The processing circuitry 301 is a processor that realizes functions corresponding to each program by reading and executing the program from the memory 303. Note that, in FIG. 1, it was described that the imaging control function 3011, the acquisition function 3012, and the fluoroscopic image storing control function 3013 are realized by a single processing circuit 301, but these functions may be realized by configuring the processing circuitry 301 by combining a plurality of independent processors and having each processor executing the program.

The imaging control function 3011 is a function that controls an overall imaging timing of the X-ray diagnosis apparatus 1 and each functions following imaging conditions etc. In the present embodiment, the imaging control function 3011 performs X-ray imaging or fluoroscopic imaging by receiving instructions to start the X-ray imaging or fluoroscopic imaging via the input interface 307.

The acquisition function 3012 is a function that acquires imaging related information obtained within a certain period of time before or after the X-ray imaging. Imaging related information is an operation contents of the input interface 307, information related to the subject such as the fluoroscopic image acquired by fluoroscopic imaging, or captured image acquired by X-ray imaging. In the present embodiment, the acquisition function 3012 acquires the operation contents of the input interface 307 as imaging related information.

The fluoroscopic image storing control function 3013 is a function that stores the fluoroscopic image captured at least one of before or after the X-ray imaging based on the imaging related information. In the present embodiment, the fluoroscopic image storing control function 3013 determined whether to store the fluoroscopic image based on the operation contents of the input interface 307 and when determined to store the fluoroscopic image in the memory 303, stores the fluoroscopic image captured before or after the X-ray imaging in the memory 303.

The memory 303 may be configured by a Random Access Memory (RAM), a semiconductor memory element such as a flash memory, a hard disk, or an optical disk etc. The memory 303 may be configured by a portable media such as a universal serial bus (USB) memory or a digital video disk (DVD). The memory 303 stores various processing programs used in the processing circuit 301 (includes application programs and operating systems (OS)), data necessary for executing the program, and conditions to store the fluoroscopic image in the memory 303 set by the user.

The display 305 displays various information. The display 305 may display the captured image or the fluoroscopic image acquired by the imaging apparatus 10 or a Graphical User Interface (GUI) to receive various input operation from an operator. The display 305 may be a Liquid Crystal Display (LCD), a Cathode Ray Tube (CRT) display, or an Electro Luminescence (EL) display etc. Note that the display 305 is equivalent to a display according to the present embodiment.

The input interface 307, for instance, receives various input operations from the user, converts the received input operation into electric signal, and outputs to the processing circuit 301. The input interface 307 may be realized by a trackball, a switch button, a mouse, a keyboard, a touchpad that performs input operations by touching an operating screen, or a touch panel display where a display screen and the touchpad are integrated, etc. The input interface 307, for instance, receives input of information about the subject P or imaging conditions etc., when imaging the subject P. The input interface 307 also has an X-ray imaging switch 3071 and a fluoroscopic imaging switch 3072. Note that the input interface 307 may be realized by two switches that may switch between a first switch that starts X-ray imaging preparation and a second switch that starts the X-ray imaging in response to the user's pressing amount.

The X-ray imaging switch 3071 is a switch to operate whether to perform X-ray imaging, i.e., whether to irradiate X-ray; and may be consisted of a hand switch. The X-ray imaging switch 3071 may also be referred to as an exposure switch. The X-ray imaging to the subject P, for instance, is performed when the X-ray imaging switch 3071 is pressed by the user until the X-ray imaging is terminated based on the imaging conditions set by the user. Note that the X-ray imaging switch 3071 may be provided in the imaging apparatus 10.

Likewise, the fluoroscopic imaging switch 3072 is a switch to operate whether to perform fluoroscopic imaging, i.e., whether to irradiate X-ray; and may be consisted of a foot switch. The fluoroscopic imaging switch 3072 may be arranged on a floor of a detecting room where the X-ray diagnosis apparatus 1 is provided. fluoroscopic imaging to the subject P, for instance, is performed when the fluoroscopic imaging switch 3072 is pressed by the user until the fluoroscopic imaging switch 3072 which was pressed is released by the user. Note that the fluoroscopic imaging switch 3072 may be provided in the imaging apparatus 10.

The output interface 309 may output signal supplied by the processing circuitry 301. The output interface 309, for instance, may be realized by an indicator such as a lamp, audio devices that outputs sound such as a speaker, or printed circuits such as a printer.

Figure 2:
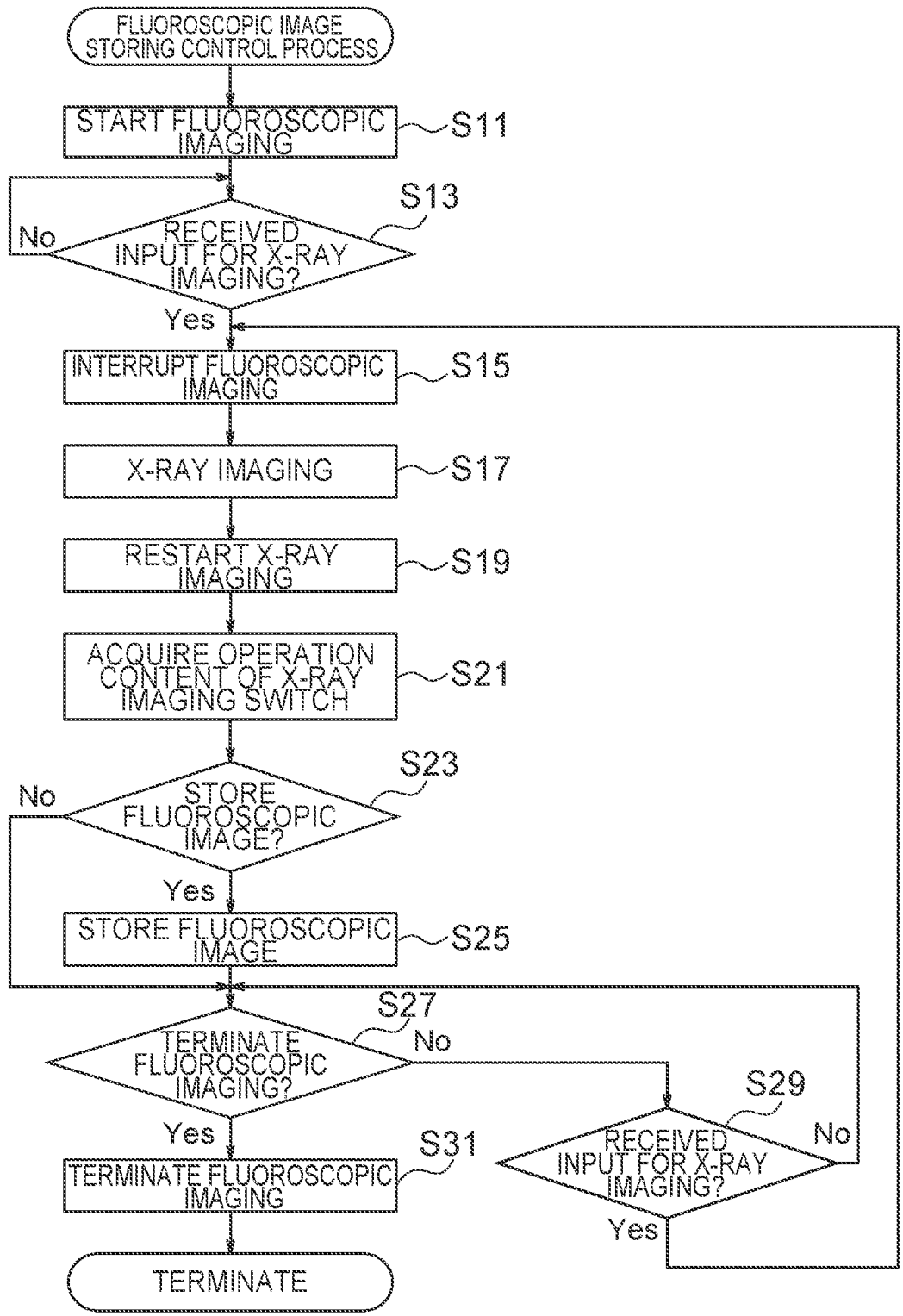
FIG. 2 is a flowchart that describes a content of a fluoroscopic image storing control process executed in the X-ray diagnosis apparatus according to the first embodiment.
Figure 3:
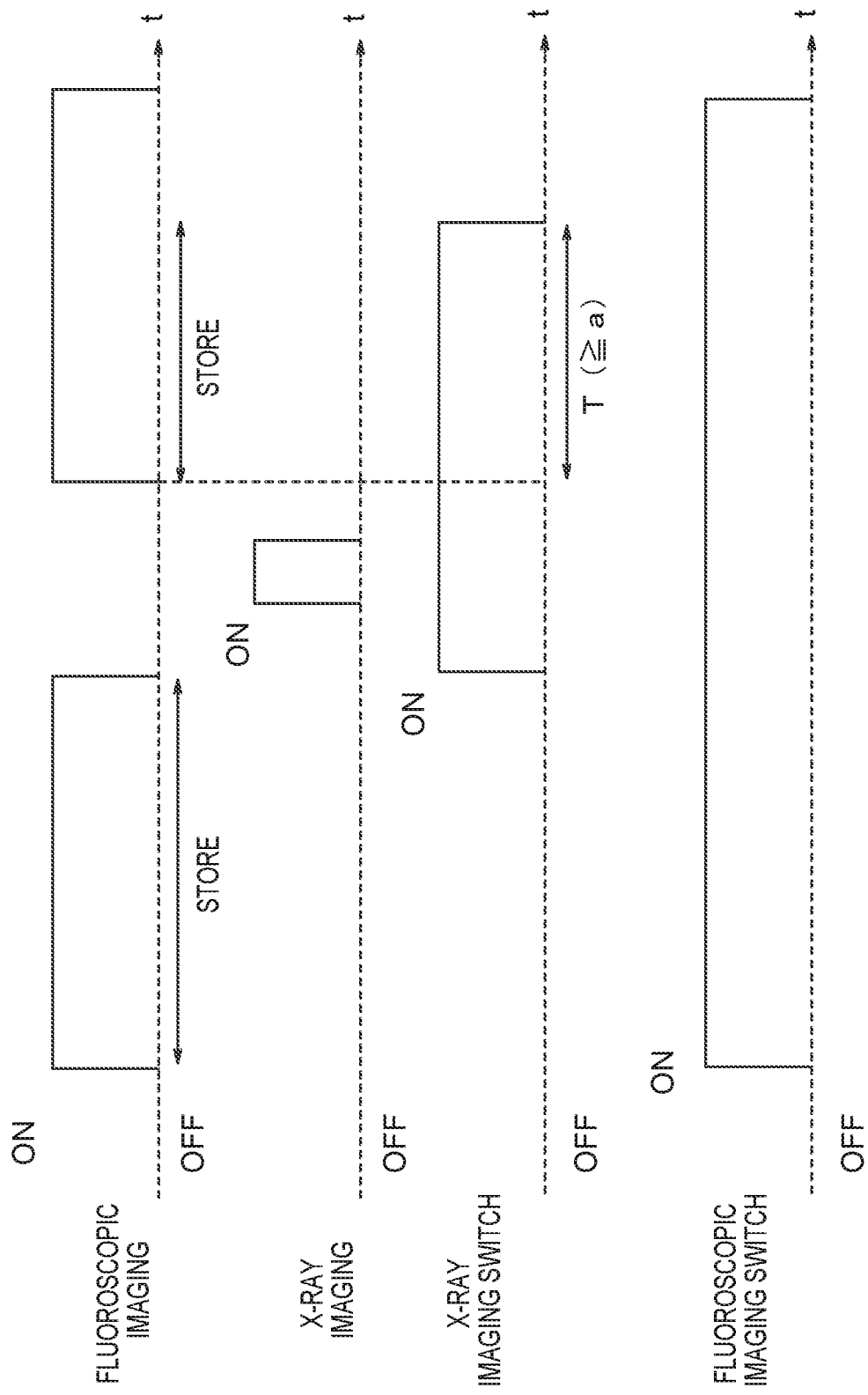
FIG. 3 is a timing chart that illustrates timings of a fluoroscopic imaging, an X-ray imaging, and storing the fluoroscopic image executed in the X-ray diagnosis apparatus according to the first embodiment.

Next, the fluoroscopic image storing control process performed in the X-ray diagnosis apparatus 1 according to the present embodiment will be described using FIGS. 2 and 3. FIG. 2 is a flowchart that describes a content of the fluoroscopic image storing control process executed in the X-ray diagnosis apparatus 1 according to the present embodiment. FIG. 3 is a timing chart that illustrates timings of the fluoroscopic imaging, the X-ray imaging, and storing the fluoroscopic image. In the fluoroscopic image storing control process shown in FIG. 2, the X-ray diagnosis apparatus 1 stores the fluoroscopic image in the memory 303 based on the operation content of the X-ray imaging switch 3071. For instance, the fluoroscopic image storing control process may be a process performed when the fluoroscopic imaging starts.

Figure 4:
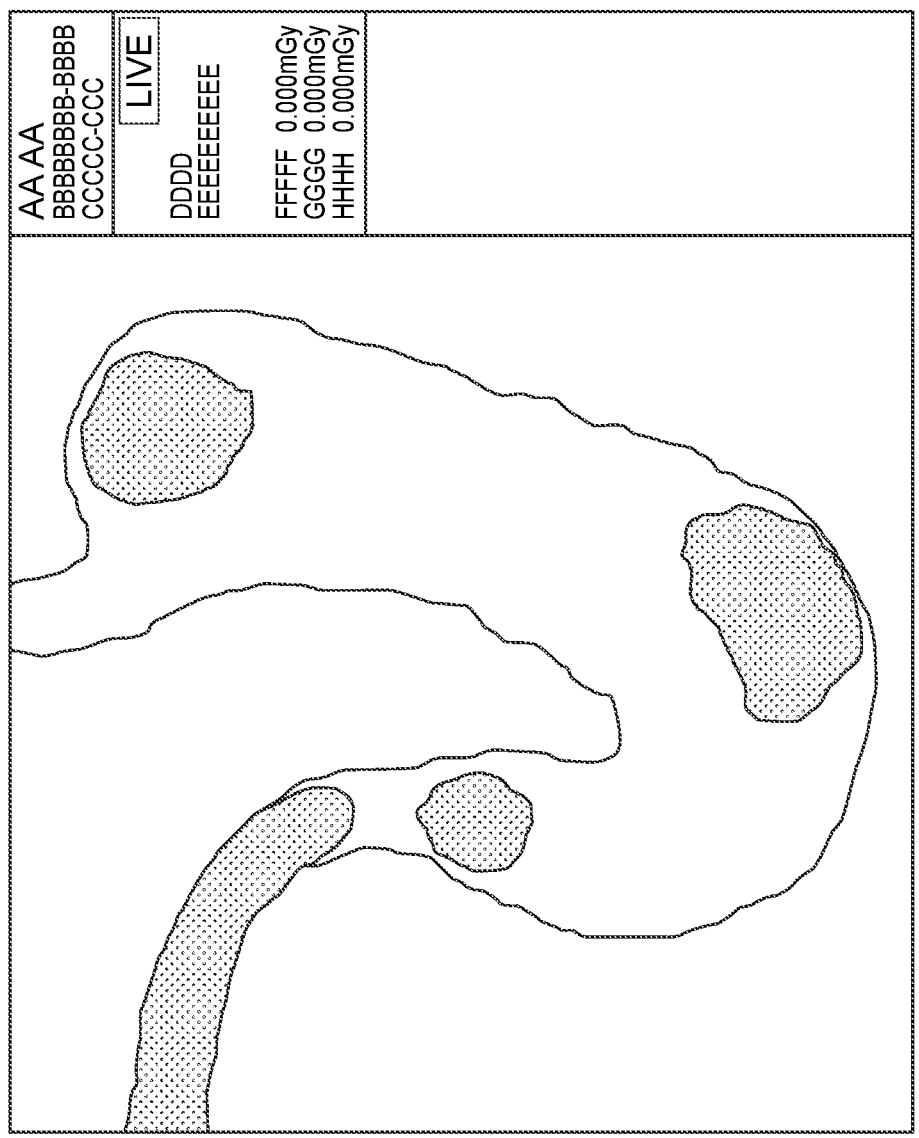
FIG. 4 is a diagram that illustrates an example of the fluoroscopic image displayed on a display of the X-ray diagnosis apparatus according to the first embodiment.

As shown in FIG. 2, the X-ray diagnosis apparatus 1 first starts fluoroscopic imaging (Step S11). The process of starting the fluoroscopic imaging is realized by the imaging control function 3011 in the processing circuitry 301. Specifically, as shown in FIG. 3, the X-ray diagnosis apparatus 1 irradiates X-ray to the subject P and starts the fluoroscopic imaging by receiving instruction to start the fluoroscopic imaging by the user. More specifically, as shown in FIG. 3, fluoroscopic imaging is turned ON and started when the fluoroscopic imaging switch 3072 is pressed. Likewise, by starting the fluoroscopic imaging, the X-ray diagnosis apparatus 1 displays the fluoroscopic image acquired by the fluoroscopic imaging on the display 305 as shown in FIG. 4. Note that the fluoroscopic imaging shown in FIG. 3 shows continuous fluoroscopic imaging that irradiates X-ray continuously to perform fluoroscopic imaging, but the fluoroscopic imaging may be the pulse fluoroscopic imaging that irradiates X-ray intermittently to perform fluoroscopic imaging.

Next, as shown in FIG. 2, the X-ray diagnosis apparatus 1 determines whether the X-ray imaging was received (Step S13). The process of determining whether the X-ray imaging was received is realized by the imaging control function 3011 in the processing circuitry 301. Specifically, the X-ray diagnosis apparatus 1 determines whether the input to start the X-ray imaging was received from the user via the X-ray imaging switch 3071. Then, when determining that the input to start the X-ray imaging was not received (Step S13: No), the X-ray diagnosis apparatus 1 repeats the process of Step S13 and standbys. That is, the X-ray diagnosis apparatus 1 continues the fluoroscopic imaging started at Step S11.

On the other hand, when determining that the input to start the X-ray imaging was received (Step S13: Yes), the X-ray diagnosis apparatus interrupts fluoroscopic imaging (Step S15). The process of interrupting the fluoroscopic imaging is realized by the imaging control function 3011 in the processing circuitry 301. Specifically, the X-ray diagnosis apparatus 1 interrupts the fluoroscopic imaging by receiving the input to start X-ray imaging via the X-ray imaging switch 3071. More specifically, as shown in FIG. 3, the X-ray diagnosis apparatus 1 starts preparing the X-ray imaging and interrupts the fluoroscopic imaging when the X-ray imaging switch 3071 is pressed. That is, as shown in FIG. 3, fluoroscopic imaging is interrupted and X-ray imaging is preferentially performed by the X-ray imaging turned ON even when fluoroscopic imaging is performed. Preparing the X-ray imaging, for instance, may be controlling a tube current or the tube voltage based on imaging conditions of X-ray imaging.

Note that if fluoroscopic imaging is interrupted, the X-ray diagnosis apparatus 1 may display on the display 305 an image of one frame of the fluoroscopic image acquired right before interrupting the fluoroscopic imaging, until the X-ray imaging is performed.

Next, as shown in FIG. 2, the X-ray diagnosis apparatus 1 performs X-ray imaging (Step S17). The process of performing X-ray imaging is realized by the imaging control function 3011 in the processing circuitry 301. Specifically, the X-ray diagnosis apparatus 1 performs X-ray imaging by irradiating X-ray to subject P.

Next, as shown in FIG. 2, the X-ray diagnosis apparatus 1 restarts fluoroscopic imaging (Step S19). The process of restarting fluoroscopic imaging is realized by the imaging control function 3011 in the processing circuitry 301. Specifically, the X-ray diagnosis apparatus 1 restarts fluoroscopic imaging by switching to fluoroscopic imaging after the X-ray imaging is terminated. More specifically, for instance, as shown in FIG. 3, the X-ray diagnosis apparatus 1 restarts fluoroscopic imaging when the X-ray imaging becomes OFF and the fluoroscopic imaging ON. Also, by restarting the fluoroscopic imaging, the X-ray diagnosis apparatus 1 displays the fluoroscopic image acquired by fluoroscopic imaging on the display 305 as shown in FIG. 4.

Next, as shown in FIG. 2, the X-ray diagnosis apparatus 1 acquires imaging related information obtained within the certain period of time before or after the X-ray imaging (Step S21). The process of obtaining image related information obtained within the certain period of time before or after the X-ray imaging is realized by the acquisition function 3012 in the processing circuitry 301. Specifically, the X-ray diagnosis apparatus 1 acquires operation contents of the X-ray imaging switch 3071 which the user operates within the certain period of time before or after the X-ray imaging, as the image related information obtained within the certain period of time before or after the X-ray imaging. More specifically, as shown in FIG. 3, the X-ray diagnosis apparatus 1, acquires a time T between when the X-ray diagnosis apparatus 1 restarts fluoroscopic imaging at Step S19 until the user releases the X-ray imaging switch 3071, i.e., between when the X-ray diagnosis apparatus 1 resumes fluoroscopic imaging until the X-ray imaging switch 3071 is turned OFF, as the operation content of the X-ray imaging switch 3071.

Note that at Step S21, the X-ray diagnosis apparatus 1 acquires time T between when the X-ray diagnosis apparatus 1 restarts fluoroscopic imaging at Step S19 until the X-ray imaging switch 3071 is released, as the operation content of the X-ray imaging switch 3071, but the operation content of the X-ray imaging switch 3071 acquired by the X-ray diagnosis apparatus 1 is not limited to such. That is, the operation content of the X-ray imaging switch 3071 is arbitrary, and for instance, may be the time between when the user presses the X-ray imaging switch 3071 until the X-ray imaging switch 3071 is released, or a time between when the X-ray imaging is terminated until the X-ray imaging switch 3071 is released. Likewise, the operation contents of the X-ray imaging switch 3071 is not limited to the time of operating the X-ray imaging switch 3071, but may be a predetermined operating manner such as a number of operating the X-ray imaging switch 3071 within the certain period of time before or after the X-ray imaging.

Next, as shown in FIG. 2, the X-ray diagnosis apparatus 1, based on the image related information, determines whether to store the fluoroscopic image (Step S23). The process of determining whether to store the fluoroscopic image is realized by the fluoroscopic image storing control function 3013 in the processing circuitry 301. Specifically, the X-ray diagnosis apparatus 1 determines whether to store the fluoroscopic image based on the operation content of the X-ray imaging switch 3071 acquired at Step S21. More specifically, the X-ray diagnosis apparatus 1 determines whether to store the fluoroscopic image in the memory 303 by comparing the time T, acquired at Step S21, between when the X-ray diagnosis apparatus 1 restarts fluoroscopic imaging until the X-ray imaging switch 3071 turns OFF, and a threshold a that is preset as a condition to store the fluoroscopic image in the memory 303, to determine whether time T is greater than threshold a.

Then, at Step S23, if time T is greater than threshold a, i.e., when determining to store the fluoroscopic image (Step S23: Yes), the X-ray diagnosis apparatus 1 stores the fluoroscopic image in the memory 303 (Step S25). The process of storing the fluoroscopic image in the memory 303 is realized by the fluoroscopic image storing control function 3013 in the processing circuitry 301. Specifically, as shown in FIG. 3, the X-ray diagnosis apparatus 1 stores the fluoroscopic image acquired between starting the fluoroscopic imaging at Step S11 until interrupting the fluoroscopic imaging at Step S15, and between restarting the fluoroscopic imaging at Step S19 until releasing the X-ray imaging switch 3071, in the memory 303.

Note that, at Step S25, the fluoroscopic image to be stored in the memory 303 is not limited to the fluoroscopic image acquired between starting the fluoroscopic imaging at Step S11 until interrupting the fluoroscopic imaging at Step S15, and between restarting the fluoroscopic imaging at Step S19 until releasing the X-ray imaging switch 3071, in the memory 303. That is, the fluoroscopic image to be stored in the memory 303 is arbitrary, and the X-ray diagnosis apparatus 1 may store the fluoroscopic image for a preset number of frames among the fluoroscopic image acquired between starting the fluoroscopic imaging at Step S11 until interrupting the fluoroscopic imaging at Step S15, and between restarting the fluoroscopic imaging at Step S19 until releasing the X-ray imaging switch 3071, in the memory 303.

Likewise, the X-ray diagnosis apparatus 1 may store either of the fluoroscopic image acquired between starting the fluoroscopic imaging at Step S11 until interrupting the fluoroscopic imaging at Step S15, and the fluoroscopic image acquired between restarting the fluoroscopic imaging at Step S19 until releasing the X-ray imaging switch 3071, in the memory 303. That is, the X-ray diagnosis apparatus 1 may store the fluoroscopic image captured either before or after the X-ray imaging. Furthermore, at Step S25, the X-ray diagnosis apparatus 1 may select at least one of either fluoroscopic image captured before or after the X-ray imaging by the fluoroscopic image storing control function 3013 and store the selected fluoroscopic image in the memory 303.

At Step S23, if time T is less than threshold a, i.e., when determining not to store the fluoroscopic image (Step S23: No), after the process of Step S25, the X-ray diagnosis apparatus 1 determines whether to terminate the fluoroscopic imaging (Step S27). The process of determining whether to terminate the fluoroscopic imaging is realized by the imaging control function 3011 in the processing circuitry 301. Specifically, the X-ray diagnosis apparatus 1 determines whether to terminate fluoroscopic imaging by determining whether the input to start fluoroscopic imaging was received from the user via the fluoroscopic imaging switch 3072.

Then, at Step S27, if the fluoroscopic imaging of the user was not received via the fluoroscopic imaging switch 3072, i.e., not terminating the fluoroscopic imaging (Step S27: No), the X-ray diagnosis apparatus 1 determines whether the X-ray imaging was received (Step S29). The step of determining whether the X-ray imaging was received is realized by the imaging control function 3011 in the processing circuitry 301. Specifically, the X-ray diagnosis apparatus 1 determines whether the input to start the X-ray imaging was received from the user via the X-ray imaging switch 3071.

Then, at Step S29, when determining that the input to start the X-ray imaging was not received from the user via the X-ray imaging switch 3071 (Step S29: No), the X-ray diagnosis apparatus 1 repeats the process of Step S27 and Step S29 and standbys. On the other hand, when determining that the input to start the X-ray imaging was received from the user via the X-ray imaging switch 3071 (Step S29: Yes), the X-ray diagnosis apparatus 1 returns to Step S15 and repeats the process from Step S15.

On the other hand, at Step S27, if the input of the fluoroscopic imaging was not received from the user via the fluoroscopic imaging switch 3072 (Step S31: Yes), the X-ray diagnosis apparatus 1 terminates the fluoroscopic imaging (Step S31). The process of terminating the fluoroscopic imaging is realized by the imaging control function 3011 in the processing circuitry 301.

By executing Step S31, the fluoroscopic image storing control process according to the present embodiment is terminated.

As described above, in the X-ray diagnosis apparatus 1 according to the present embodiment, since the X-ray diagnosis apparatus 1 acquires the operation content of the X-ray imaging switch 3071 as the image related information acquired within the certain period of time before or after the X-ray imaging, determines whether to store in the memory 303 the fluoroscopic image captured before or after the X-ray imaging based on the operation content of the X-ray imaging switch 3071, and stores the fluoroscopic image captured before or after the fluoroscopic imaging in the memory 303 when determining to store the fluoroscopic image captured before or after the X-ray imaging in the memory 303, the fluoroscopic image may be stored in a simple and appropriate manner. That is, in the present embodiment, since the X-ray diagnosis apparatus 1 stores the fluoroscopic image in the memory 303 when pressing the X-ray imaging switch 3071 which the user presses to perform X-ray imaging even after the X-ray imaging is terminated, and the time T of pressing the X-ray imaging switch 3071 after the X-ray imaging is greater than the preset threshold a, the user may store the necessary fluoroscopic image without performing operations other than imaging operations.

Note that in the present embodiment described above, the X-ray diagnosis apparatus 1 acquired the operation content of the X-ray imaging switch 3071, but the operation contents which the X-ray diagnosis apparatus 1 acquires is not limited to the X-ray imaging switch 3071. That is, a target of the operation content which the X-ray diagnosis apparatus 1 acquires is arbitrary, and for instance, may be the operation content of the fluoroscopic imaging switch 3072, or the operation content of the input interface 307 other than the X-ray imaging switch 3071 or the fluoroscopic imaging switch 3072.

[First Modification]

In the X-ray diagnosis apparatus 1 according to the first embodiment described above, it is possible to determine the number of frames to store in the memory 303 in response to an operation time of the X-ray imaging switch 3071 and store in the memory 303 the fluoroscopic image for the determined number of frames, instead of storing in the memory 303 the fluoroscopic image acquired between starting the fluoroscopic imaging until interrupting the fluoroscopic imaging and between restarting the fluoroscopic imaging until releasing the X-ray imaging switch 3071. With a first modification where the modification is applied to the first embodiment described above, parts that differ from the first embodiment will be described below. Note that the configuration of the X-ray diagnosis apparatus 1 according to the first modification is equivalent to that of FIG. 1, and description will be omitted.

Figure 5:
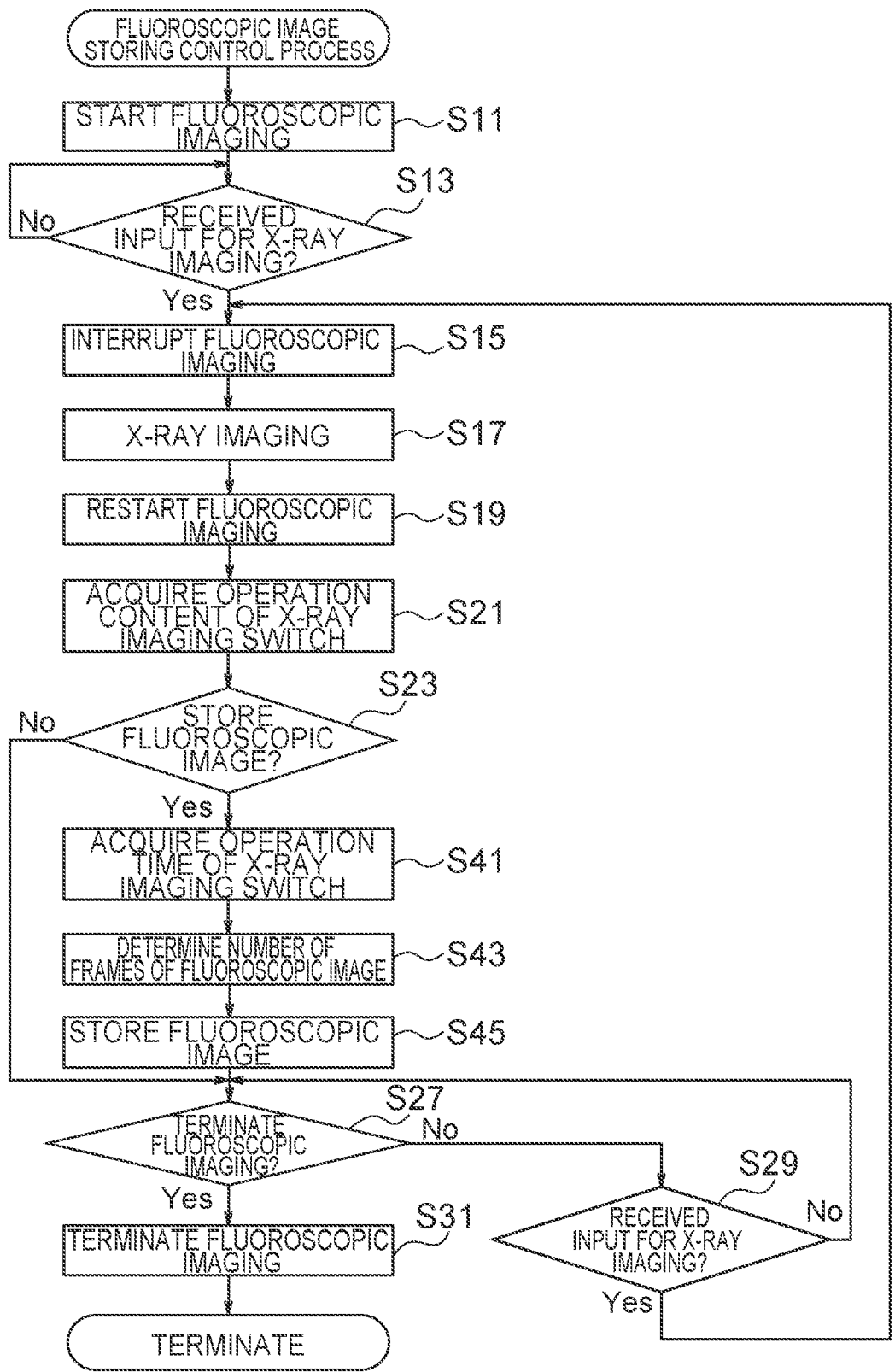
FIG. 5 is a flowchart that describes a content of the fluoroscopic image storing control process executed in the X-ray diagnosis apparatus according to a first modification.
Figure 6:
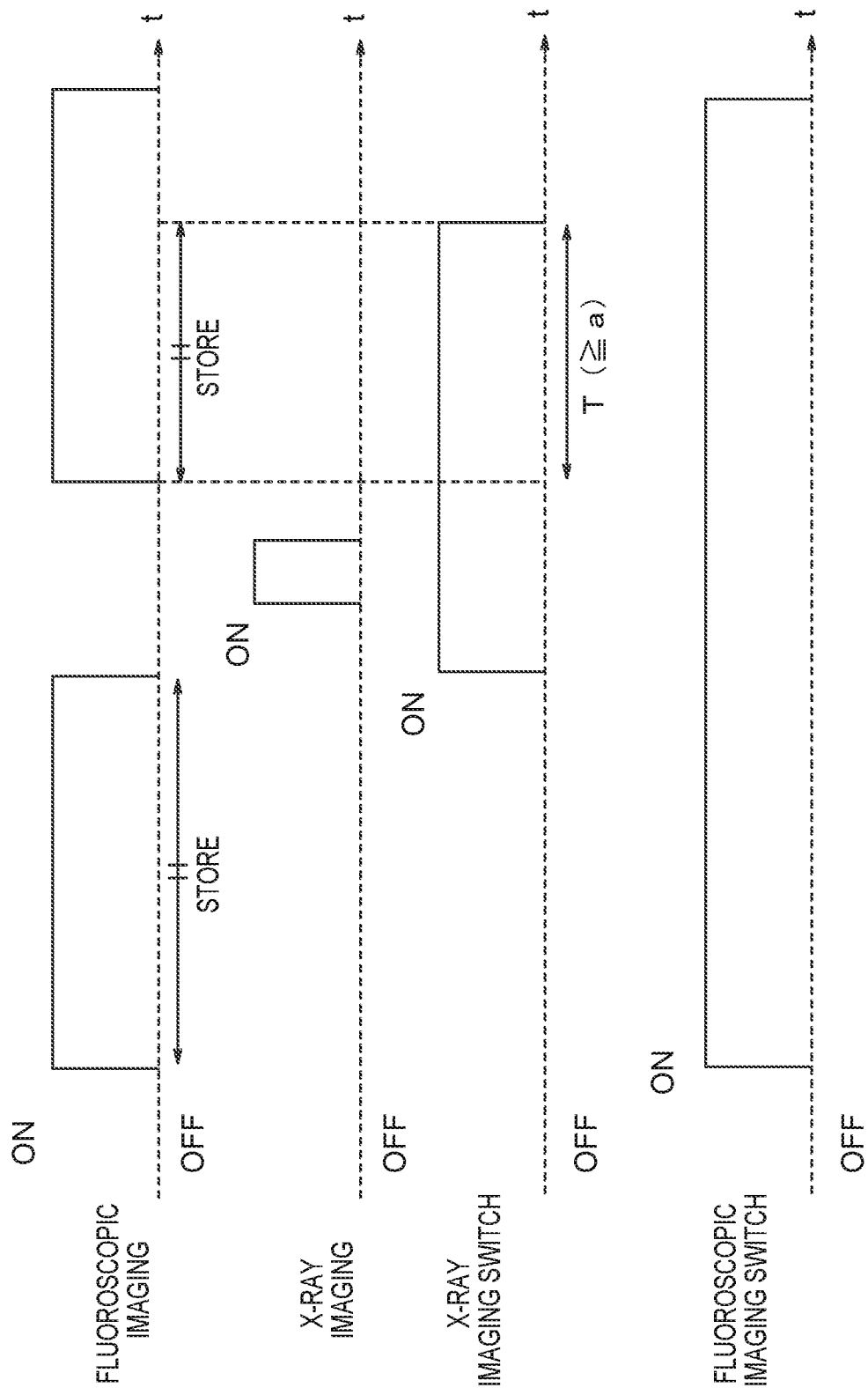
FIG. 6 is a timing chart that illustrates timings of a fluoroscopic imaging, an X-ray imaging, and storing the fluoroscopic image executed in the X-ray diagnosis apparatus according to the first modification.

Next, the fluoroscopic image storing control process executed in the X-ray diagnosis apparatus 1 according to the first modification will be described using FIGS. 5 and 6. FIG. 5 is a flowchart that describes a content of the fluoroscopic image storing control process executed in the X-ray diagnosis apparatus 1 according to the first modification, which corresponds to FIG. 2 of the first embodiment described above. FIG. 6 is a timing chart that illustrates timings of a fluoroscopic imaging, an X-ray imaging, and storing the fluoroscopic image according to the first modification, which corresponds to FIG. 3 of the first embodiment described above. In the fluoroscopic image storing control process shown in FIG. 5, the X-ray diagnosis apparatus 1 determines the number of frames to store in the memory 303 or store the fluoroscopic image for the determined number of frames based on the operation content of the X-ray imaging switch 3071. For instance, the fluoroscopic image storing control process is a process executed when the fluoroscopic imaging starts. Note that the process before Step S23 shown in FIG. 5 is equivalent to that of FIG. 2 described above, and description will be omitted.

Then, at Step S23, if time T is greater than the threshold a, i.e., when determining to store the fluoroscopic image (Step S23: Yes), the X-ray diagnosis apparatus 1 acquires the operation time of the X-ray imaging switch 3071 (Step S41). The process of acquiring the operation time of the X-ray imaging switch 3071 is realized by the fluoroscopic image storing control function 3013 in the processing circuitry 301. Specifically, as shown in FIG. 6, the X-ray diagnosis apparatus 1 acquires the time between when the X-ray diagnosis apparatus 1 restarts the fluoroscopic imaging at Step S19 until the user releases the X-ray imaging switch 3071, i.e., time T between when the X-ray diagnosis apparatus 1 restarts fluoroscopic imaging until the X-ray imaging switch 3071 is turned OFF.

Note that the X-ray diagnosis apparatus 1 acquired time T between when the X-ray diagnosis apparatus 1 restarts fluoroscopic imaging at Step S19 until releasing the X-ray imaging switch 3071 as the operation time of the X-ray imaging switch 3071, but the operation time of the X-ray imaging switch 3071 which the X-ray diagnosis apparatus 1 acquires is not limited to this. That is, the operation time of the X-ray imaging switch 3071 is arbitrary, and for instance, may be the time between pressing and releasing the X-ray imaging switch 3071 by the user, or may be the time between terminating the X-ray imaging and releasing the X-ray imaging switch 3071. Also, at Step S21, when acquiring the operation time of the X-ray imaging switch 3071 as the operation content of the X-ray imaging switch 3071, Step S41 is omitted.

Next, as shown in FIG. 5, the X-ray diagnosis apparatus 1 determines the number of frames of the fluoroscopic image to store in the memory 303 (Step S43). The process of determining the number of frames of the fluoroscopic image is realized by the fluoroscopic image storing control function 3013 in the processing circuitry 301. Specifically, the X-ray diagnosis apparatus 1 determines the number of frames of the fluoroscopic image to store in the memory 303 in response to the operation time of the X-ray imaging switch 3071 acquired at Step S41.

More specifically, as shown in FIG. 6, the X-ray diagnosis apparatus 1 determines the number of frames of the fluoroscopic image equivalent to time T before interrupting the fluoroscopic imaging among the fluoroscopic image acquired between starting the fluoroscopic imaging at Step S11 and interrupting the fluoroscopic imaging at Step S15, and the number of frames of the fluoroscopic image equivalent to time T after restarting the fluoroscopic imaging among the fluoroscopic image acquired between restarting the fluoroscopic imaging and terminating the fluoroscopic imaging, as the number of frames of the fluoroscopic image to store in the memory 303 in response to time T, which is the operation time of the X-ray imaging switch 3071, between when the X-ray diagnosis apparatus 1 restarts fluoroscopic imaging until the X-ray imaging switch 3071 is turned OFF. In the example shown in FIG. 6, the number of frames of the fluoroscopic image equivalent to time T before interrupting the fluoroscopic imaging among the fluoroscopic image acquired between starting the fluoroscopic imaging at Step S11 and interrupting the fluoroscopic imaging at Step S15, and the number of frames of the fluoroscopic image equivalent to time T after restarting the fluoroscopic imaging among the fluoroscopic image acquired between restarting the fluoroscopic imaging and terminating the fluoroscopic imaging are the same.

Note that the X-ray diagnosis apparatus 1, for instance, may determine the number of frames of the fluoroscopic image equivalent to time 1.5T before interrupting the fluoroscopic imaging among the fluoroscopic image acquired between starting the fluoroscopic imaging at Step S11 and interrupting the fluoroscopic imaging at Step S15, and the number of frames of the fluoroscopic image equivalent to time 0.5T after restarting the fluoroscopic imaging among the fluoroscopic image acquired between restarting the fluoroscopic imaging and terminating the fluoroscopic imaging, as the number of frames of the fluoroscopic image to store in the memory 303.

Also, at Step S43, the X-ray diagnosis apparatus 1 stored in the memory 303 the number of frames of the fluoroscopic image equivalent to time T in response to the acquired time T, but the number of frames to store in the memory 303 may not be equivalent to time T. That is, the number of frames of the fluoroscopic image to store in the memory 303 is arbitrary, and the number of frames of the fluoroscopic image before interrupting the fluoroscopic imaging among the fluoroscopic image acquired between starting the fluoroscopic imaging at Step S11 and interrupting the fluoroscopic imaging at Step S15, and the number of frames of the fluoroscopic image after restarting the fluoroscopic imaging among the fluoroscopic image acquired between restarting the fluoroscopic imaging and terminating the fluoroscopic imaging, may not depend on time T but be different.

Next, as shown in FIG. 5, the X-ray diagnosis apparatus 1 stores the fluoroscopic image in the memory 303 (Step S45). The process of storing the fluoroscopic image in the memory 303 is realized by the fluoroscopic image storing control function 3013 in the processing circuitry 301. Specifically, the X-ray diagnosis apparatus 1 store the fluoroscopic image in the memory 303 by the number of frames of the fluoroscopic image determined at Step S43. Note that Steps S27 to S31 after Step S45 is equivalent to that of FIG. 2 in the first embodiment, and description will be omitted. Then, by executing Step S31, the fluoroscopic image storing control process according to the first modification is terminated.

As described above, since the X-ray diagnosis apparatus 1 according to the present modification acquires the operation time of the X-ray imaging switch 3071, determines the number of frames of the fluoroscopic image to store in the memory 303 in response to the operation time of the X-ray imaging switch 3071 that is acquired, and stores the determined number of frames of the fluoroscopic image in the memory 303, necessary fluoroscopic image may be stored while reducing oppression on the memory without additional operations other than the imaging operation. That is, fluoroscopic image may be stored in an appropriate and simple manner.

Note that, in the present modification, the X-ray diagnosis apparatus 1 determined the number of frames to store in the memory 303 in response to the time of operating the X-ray imaging switch 3071, but the operation target when determining the number of frames is not limited to the X-ray imaging switch 3071. That is, the operation target when determining the number of frames is arbitrary, and for instance, may be the operation time of the fluoroscopic imaging switch 3072 or the operation time of the input interface 307 other than the X-ray imaging switch 3071 or the fluoroscopic imaging switch 3072.

[Second Modification]

In the X-ray diagnosis apparatus 1 according to the first embodiment described above, it is possible to store in the memory 303 the fluoroscopic image captured at least one of before or after the X-ray imaging, instead of storing in the memory 303 the fluoroscopic image captured both before or after the X-ray imaging. With a second modification where the modification is applied to the first embodiment described above, parts that differ from the first embodiment will be described below. Note that the configuration of the X-ray diagnosis apparatus 1 according to the second modification is equivalent to that of FIG. 1, and description will be omitted.

Figure 7:
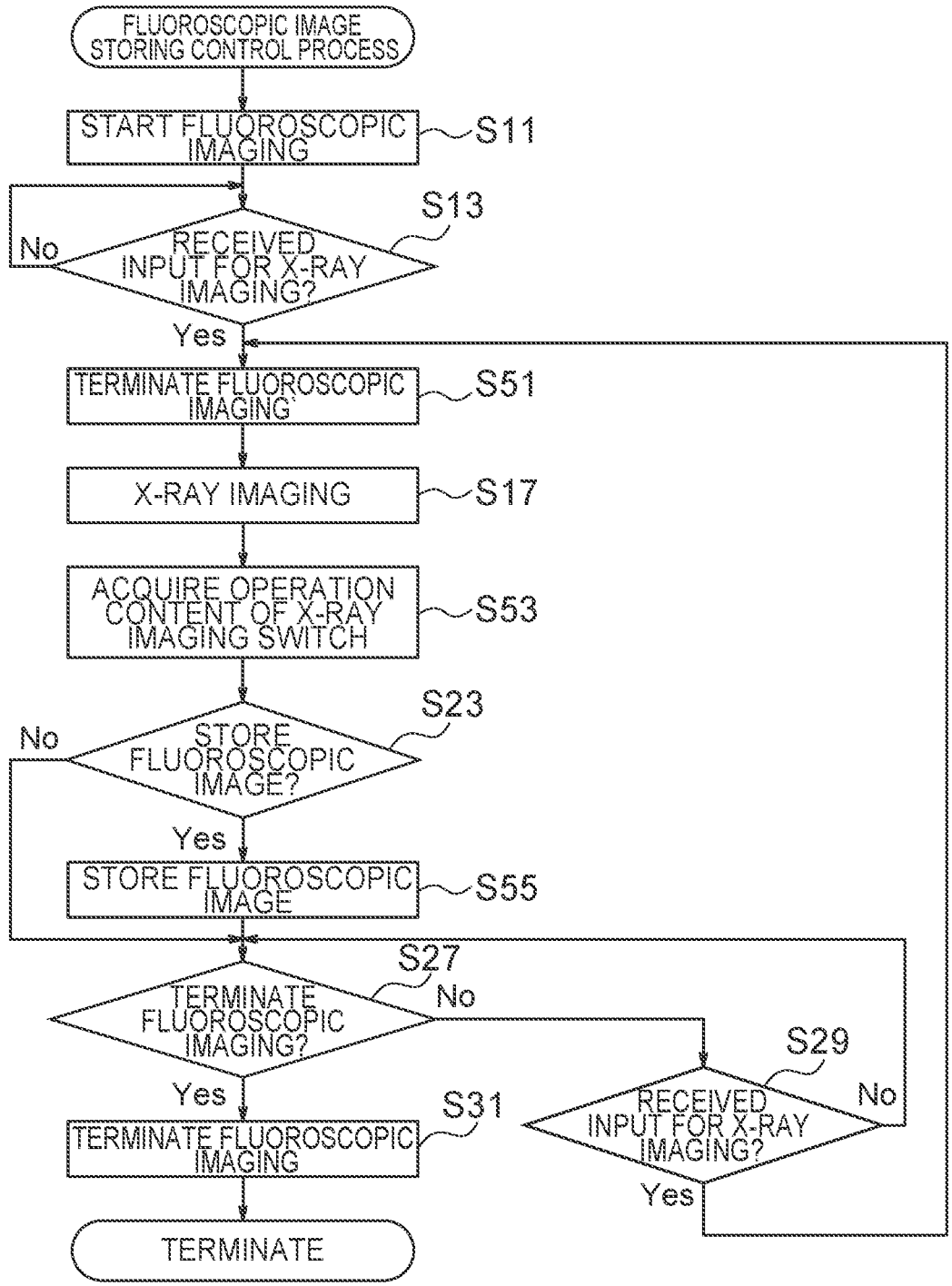
FIG. 7 is a flowchart that describes a content of the fluoroscopic image storing control process executed in the X-ray diagnosis apparatus according to a second modification.
Figure 8:
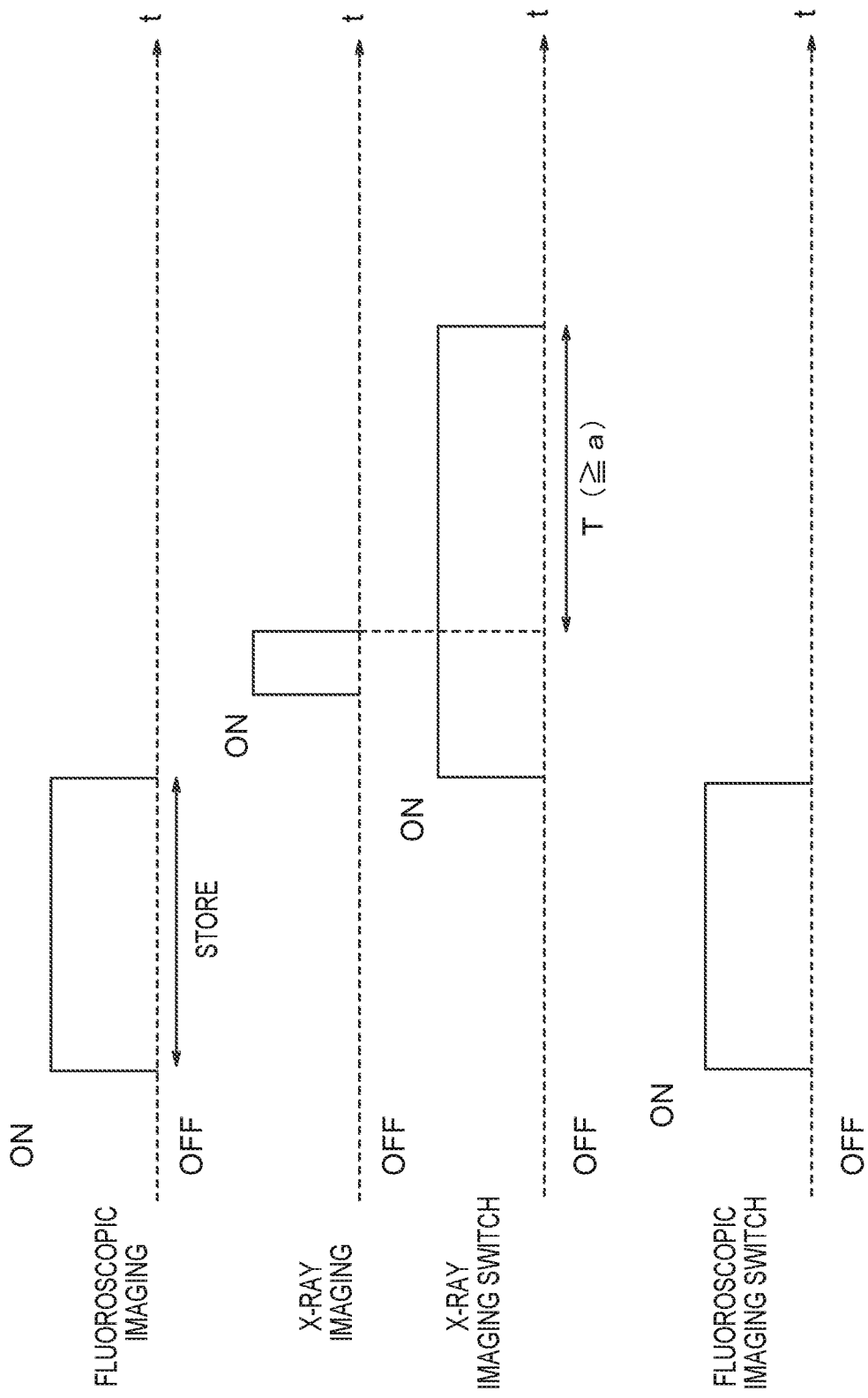
FIG. 8 is a timing chart that illustrates timings of a fluoroscopic imaging, an X-ray imaging, and storing the fluoroscopic image executed in the X-ray diagnosis apparatus according to the second modification.

Next, the fluoroscopic image storing control process executed in the X-ray diagnosis apparatus 1 according to the second modification will be described using FIGS. 7 and 8. FIG. 7 is a flowchart that describes a content of the fluoroscopic image storing control process executed in the X-ray diagnosis apparatus 1 according to the second modification, which corresponds to FIG. 2 of the first embodiment described above. FIG. 8 is a timing chart that illustrates timings of a fluoroscopic imaging, an X-ray imaging, and storing the fluoroscopic image according to the second modification, which corresponds to FIG. 3 of the first embodiment described above. In the fluoroscopic image storing control process shown in FIG. 7, the X-ray diagnosis apparatus 1 stores in the memory 303 the fluoroscopic image captured before the X-ray imaging based on an operation content of the X-ray imaging switch 3071. For instance, the fluoroscopic image storing control process may be a process executed when the fluoroscopic imaging starts. Note that the process of Steps S11 and S13 shown in FIG. 7 is equivalent to that of FIG. 2 described above, and description will be omitted.

On the other hand, at Step S13, if the X-ray diagnosis apparatus 1 determines that the input to start X-ray imaging was received, the X-ray diagnosis apparatus 1 terminates the fluoroscopic imaging (Step S51). The process of terminating the fluoroscopic imaging is realized by the imaging control function 3011 in the processing circuitry 301. Specifically, the X-ray diagnosis apparatus 1 terminates fluoroscopic imaging by receiving the input to start the X-ray imaging via the X-ray imaging switch 3071. More specifically, as shown in FIG. 3, the X-ray diagnosis apparatus 1 starts X-ray imaging preparation and terminates when the X-ray imaging switch 3071 is pressed. Note that, the process of Step S17 after Step S51 is equivalent to that of FIG. 2 in the first embodiment described above, and description will be omitted.

Next, as shown in FIG. 7, the X-ray diagnosis apparatus 1 acquires the image related information obtained within the certain period of time before or after the X-ray imaging (Step S53). The step of acquiring the image related information obtained within the certain period of time before or after the X-ray imaging is realized by the acquisition function 3012 in the processing circuitry 301. Specifically, the X-ray diagnosis apparatus 1 acquires the operation content of the X-ray imaging switch 3071 which the user operates within the certain period of time before or after the X-ray imaging, as the image related information obtained within the certain period of time. More specifically, as shown in FIG. 7, the X-ray diagnosis apparatus 1 acquires time T between when the X-ray imaging is terminated at Step S17 until the user releases the X-ray imaging switch 3071, i.e., between when the X-ray imaging is terminated at Step S17 until the X-ray imaging switch 3071 is turned OFF. Note that the process of Step S23 after Step S53 is equivalent to that of FIG. 2 in the first embodiment described above, and description will be omitted.

Likewise, the X-ray diagnosis apparatus 1 acquired the time between when the X-ray imaging is terminated at Step S17 until the user releases the X-ray imaging switch 3071, as the operation content of the X-ray imaging switch, but the operation content of the X-ray imaging switch 3071 acquired by the X-ray diagnosis apparatus 1 is not limited to this. That is, the content of the X-ray imaging switch 3071 is arbitrary, and for instance, may be the time between pressing and releasing the X-ray imaging switch 307. Likewise, the operation content of the X-ray imaging switch 3071 is not limited to the time of operating the X-ray imaging switch 3071, but may be preset aspect of operation of the X-ray imaging switch 3071, such as the number of times of operating the X-ray imaging switch 3071 within the certain period of time before or after the X-ray imaging.

Then, at Step S23, if time T is greater than threshold a, i.e., when determining to store the fluoroscopic image in the memory (Step S23: Yes), the X-ray diagnosis apparatus 1 stores the fluoroscopic image in the memory 303 (Step S55). The process of storing the fluoroscopic image in the memory is realized by the fluoroscopic image storing control function 3013 in the processing circuitry 301. Specifically, the X-ray diagnosis apparatus 1 stores in the memory 303 the fluoroscopic image acquired between starting the fluoroscopic imaging at Step S11 and terminating the fluoroscopic imaging at Step S51.

Note that, at Step S25, the fluoroscopic image to be stored in the memory 303 is not limited to the fluoroscopic image acquired between starting the fluoroscopic imaging at Step S11 and terminating the fluoroscopic imaging at Step S51. That is, the fluoroscopic image to be stored in the memory 303 is arbitrary, and for instance, may store the fluoroscopic image for the predetermined number of frames in the memory 303, among the fluoroscopic image acquired between starting fluoroscopic imaging at Step S11 until terminating the fluoroscopic imaging at Step S51, or if the fluoroscopic image captured before or after the X-ray imaging is acquired, acquire both the fluoroscopic image captured before or after the X-ray imaging, similar to the first embodiment described above.

Steps S27 to S31 after Step S55 are equivalent to that of FIG. 2 in the first embodiment described above, and description will be omitted. Then, by executing Step S31, the fluoroscopic image storing control process according to the second modification of the first embodiment is terminated.

As described above, since the X-ray diagnosis apparatus 1 according to the present modification, acquires time T between terminating the X-ray imaging at Step S17 and the user releasing the X-ray imaging switch 3071 as the operation content of the X-ray imaging switch as the image related information obtained within the certain period of time before or after the X-ray imaging, compares time T with the preset threshold a, and if time T is greater than the threshold a, stores the fluoroscopic image captured before the X-ray imaging in the memory 303, the fluoroscopic image may be stored in an appropriate and simple manner. That is, in the present modification, since it is possible to store the fluoroscopic image captured before the X-ray imaging in the memory 303 by continuing to press the X-ray imaging switch 3071 which the user presses to perform the X-ray imaging even after the X-ray imaging is terminated, necessary fluoroscopic image may be stored while reducing oppression on the memory without additional operations other than the imaging operation.

Note that the description of the second modification described above is a description for a case applied to the first embodiment, it is clear that the present modification may be applied to the first modification of the first embodiment. Likewise, in the present modification, the X-ray diagnosis apparatus 1 acquired the operation content of the X-ray imaging switch 3071, but the target of the operation content is not limited to that of the X-ray imaging switch 3071. That is, the target of the operation content which the X-ray diagnosis apparatus 1 acquires is arbitrary, and for instance, may be the operation content of the fluoroscopic imaging switch 3072, or the operation content of the input interface 307 other than the X-ray imaging switch 3071 or the fluoroscopic imaging switch 3072.

Second Embodiment

The X-ray diagnosis apparatus 1 according to the first embodiment described above determined whether to store the fluoroscopic image in the memory 303 as the image related information based on the operation content of the X-ray imaging switch 3071 operated within the certain period of time before or after the X-ray imaging, but embodiments are not limited to this. In the second embodiment, the X-ray diagnosis apparatus 1 may acquire the fluoroscopic image as the image related information and determine whether to store the fluoroscopic image in the memory 303 based on a result of an image analysis of the acquired fluoroscopic image. Parts that differ from that of the first embodiment will be described below.

Figure 9:
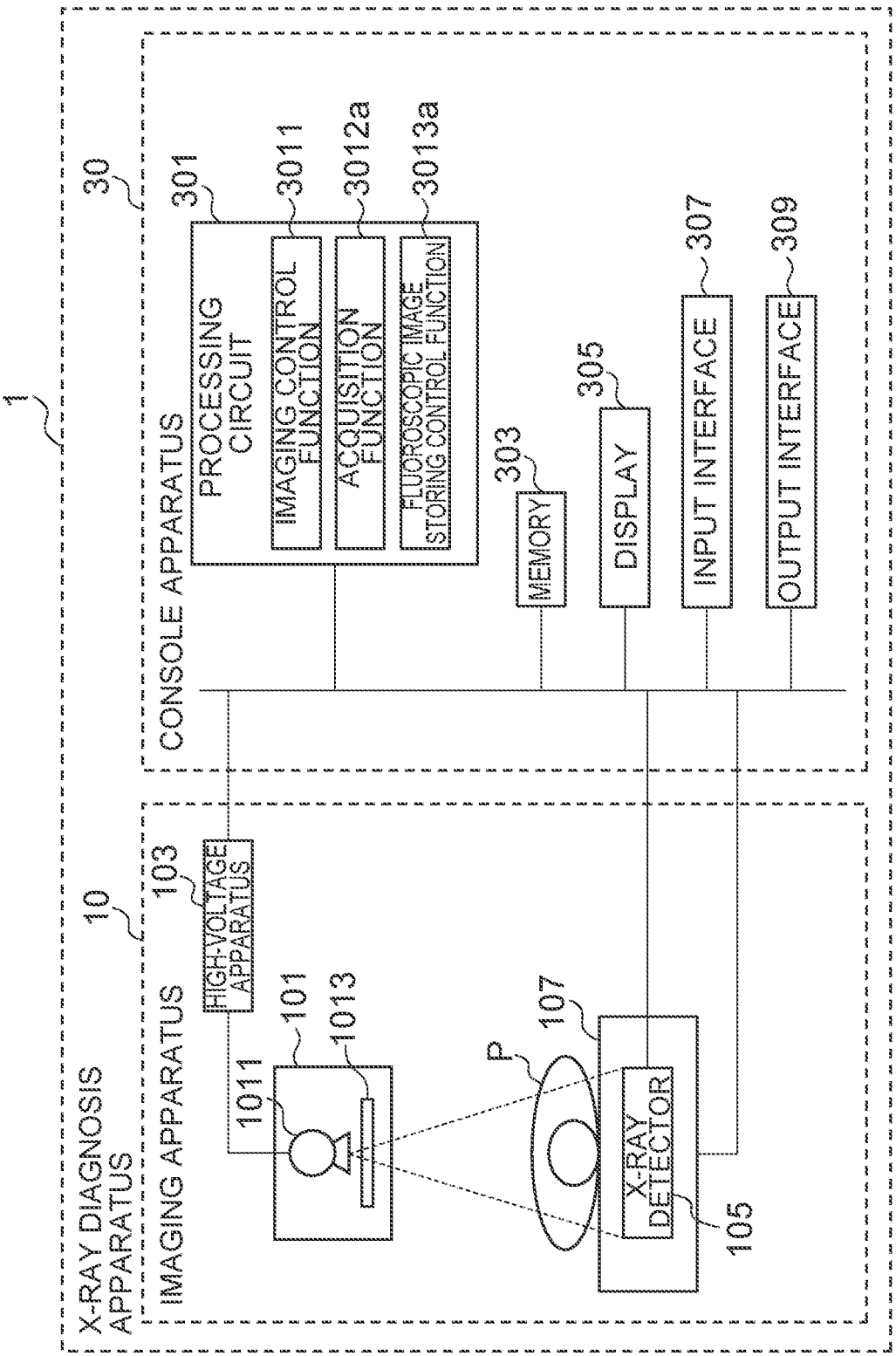
FIG. 9 is a block diagram that illustrates an exemplary configuration of the X-ray diagnosis apparatus according to a second embodiment.

FIG. 9 is a block diagram that illustrates an exemplary configuration of the X-ray diagnosis apparatus 1 according to the second embodiment, which corresponds to FIG. 1 of the first embodiment described above. As shown in FIG. 9, in the present embodiment, the functions of the acquisition function and the fluoroscopic image storing control function differ from that of the first embodiment and will be denoted as the acquisition function 3012a and the fluoroscopic image storing control function 3013a. Note that the configuration and functions other than the acquisition function 3012a and the fluoroscopic image storing control function 3013a are equivalent to that of FIG. 1 in the first embodiment, and description will be omitted.

The acquisition function 3012a is a function that acquires the image related information obtained within the certain period of time before or after the X-ray imaging. In the present embodiment, the acquisition function 3012a acquires the fluoroscopic image captured either at least one of before or after the X-ray imaging.

The fluoroscopic image storing control function 3013a is a function that stores in the memory 303 the fluoroscopic image captured either at least one of before or after the X-ray imaging based on the image related information. In the present embodiment, the fluoroscopic image storing control function 3013a performs the image analysis of the fluoroscopic image, determines whether to store the fluoroscopic image captured either at least one of before or after the X-ray imaging based on the result of the image analysis, and if determined to store the fluoroscopic image in the memory 303, stores the fluoroscopic image in the memory 303.

Figure 10:
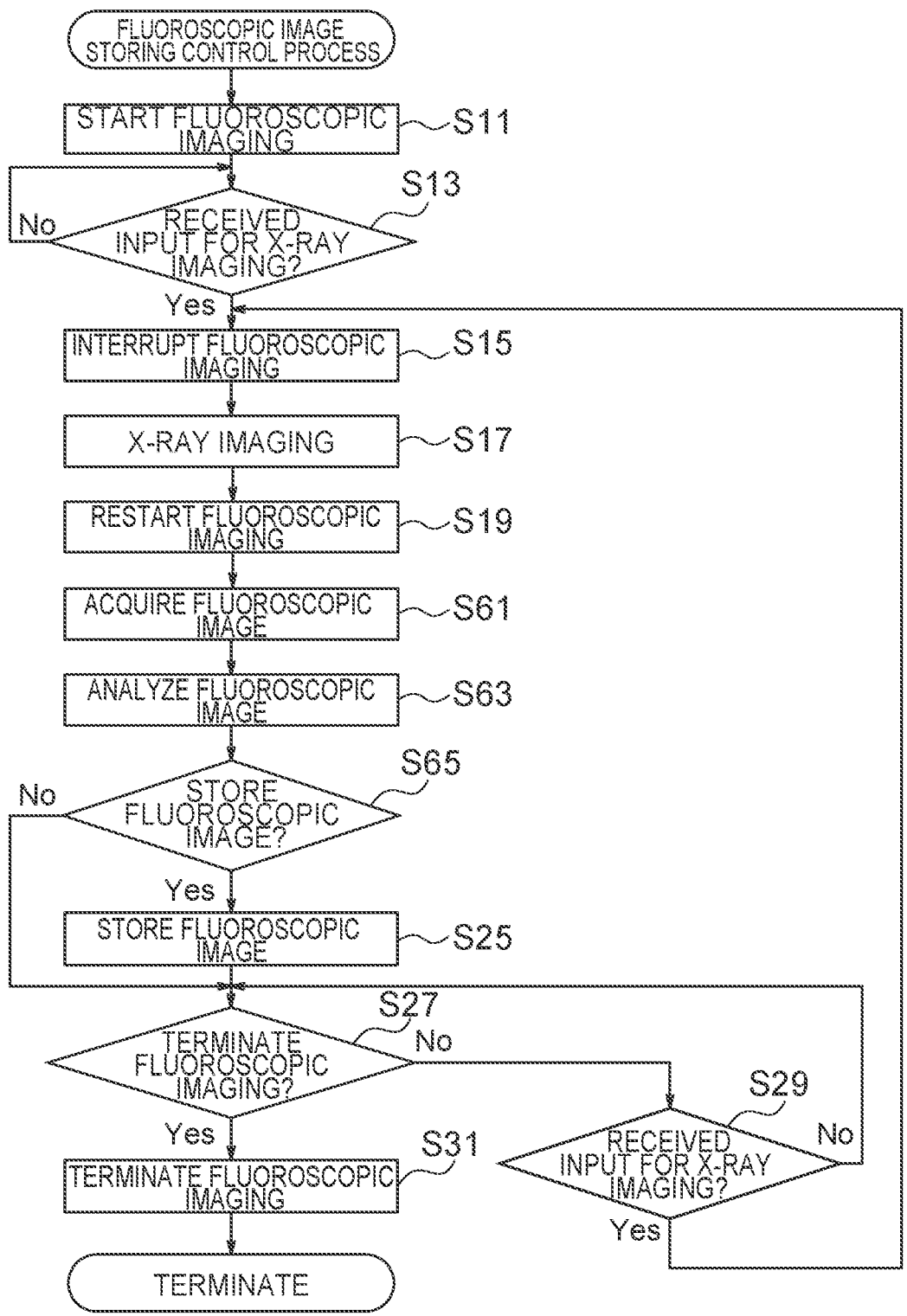
FIG. 10 is a flowchart that describes a content of the fluoroscopic image storing control process executed in the X-ray diagnosis apparatus according to the second embodiment.

Next, the fluoroscopic image storing control process that stores the fluoroscopic image, executed in the X-ray diagnosis apparatus 1 according to the present embodiment will be described using FIG. 10. FIG. 10 is a flowchart that describes a content of the fluoroscopic image storing control process executed in the X-ray diagnosis apparatus 1 according to the present embodiment, which corresponds to FIG. 1 of the first embodiment described above. In the fluoroscopic image storing control process shown in FIG. 10, the X-ray diagnosis apparatus 1 image analyzes the fluoroscopic image and determines whether to store the fluoroscopic image in the memory 303 based on the result of the analysis result of the fluoroscopic image. For instance, the fluoroscopic image storing control process is a process executed when the fluoroscopic imaging starts. Note that the process before Step S19 shown in FIG. 9 is equivalent to that of FIG. 2 in the first embodiment described above, and description will be omitted.

Next, as shown in FIG. 10, the X-ray diagnosis apparatus 1 acquires the fluoroscopic image as the image related information (Step S61). The process of acquiring the fluoroscopic image is realized by the acquisition function 3012a in the processing circuitry 301. Specifically, the X-ray diagnosis apparatus 1 acquires a plurality of fluoroscopic images among the fluoroscopic images acquired between starting the fluoroscopic imaging at Step S11 and interrupting the fluoroscopic imaging at Step S15 and the fluoroscopic images acquired within the certain period from Step S19.

Next, as shown in FIG. 10, the X-ray diagnosis apparatus 1 image analyzes the fluoroscopic image (Step S63). The process of image analyzing the fluoroscopic image is realized by the fluoroscopic image storing control function 3013a in the processing circuitry 301. Specifically, the X-ray diagnosis apparatus 1 image analyzes the plurality of fluoroscopic images acquired at Step S61. More specifically, the X-ray diagnosis apparatus 1 detects the movement of the target on the fluoroscopic image by image analyzing the fluoroscopic image acquired at Step S61.

Figure 11:
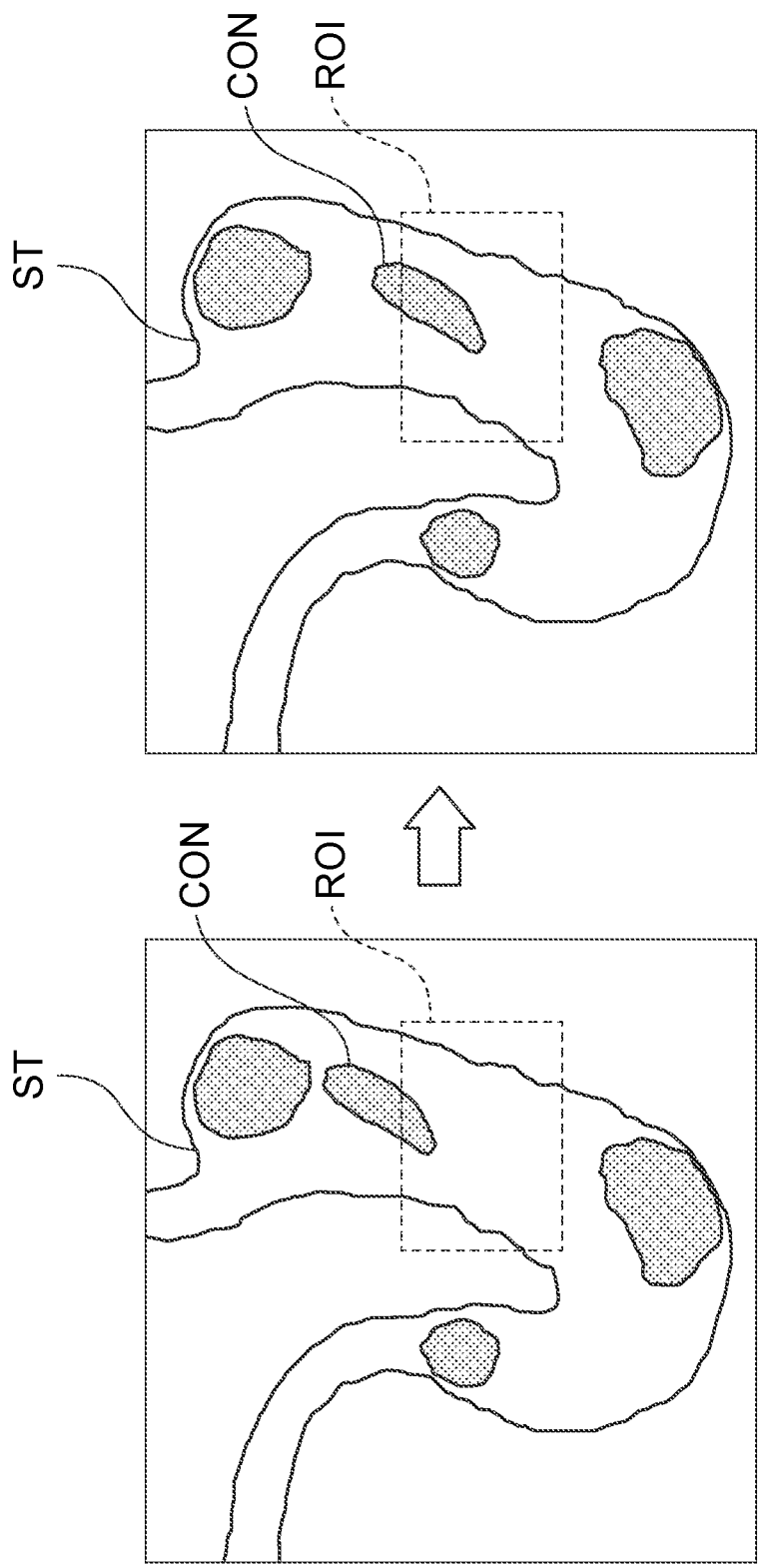
FIG. 11 is a schematic diagram that schematically illustrates a content of the fluoroscopic image storing control process executed in the X-ray diagnosis apparatus according to the second embodiment.

An example of the image analysis performed at Step S63 will be described using FIG. 11. FIG. 11 is an exemplary diagram that describes an exemplary image analysis executed in the X-ray diagnosis apparatus 1 according to the present embodiment; FIG. 11(a) is the fluoroscopic image one frame before right before interrupting the fluoroscopic imaging; and FIG. 11(b) is the fluoroscopic image right before interrupting the fluoroscopic imaging. In the example shown in FIG. 11, the fluoroscopic image is the fluoroscopic image that fluoroscopically imaged the stomach ST of the subject P, a region surrounded by a dotted line is an exemplary region of interest ROI of the user, and a dot-shaped hatching portion within the fluoroscopic image is a contrast agent CON inserted within the target stomach ST.

For instance, as shown in FIG. 11, in an imaging using the contrast agent CON such as barium, since there is a possibility of the contrast agent CON inputting the user's region of interest when performing X-ray imaging when the contrast agent CON moves within the stomach ST, the user may decide to observe the fluoroscopic image that is fluoroscopically imaged before or after the X-ray imaging when the contrast agent CON is moving. For this reason, in the example shown in FIG. 11 at Step S63, the X-ray diagnosis apparatus 1 calculates a motion vector of the contrast agent CON within the region of interest ROI of the fluoroscopic image for two frames by image analysis based on the fluoroscopic image for two frames right before interrupting the fluoroscopic imaging. That is, the X-ray diagnosis apparatus 1 calculates a movement amount of the contrast agent CON within the region of interest ROI based on the fluoroscopic image for two frames right before interrupting the fluoroscopic imaging.

Note that the region of interest ROI is a part of the fluoroscopic image in the example shown in FIG. 11, but the region of interest ROI is not limited to be the part of the fluoroscopic image. That is, the region of interest ROI is arbitrary, and for instance, may be the whole fluoroscopic image or multiple locations on the fluoroscopic image.

Likewise, in the example shown in FIG. 11, with the stomach ST as the imaging target, the image analysis of the fluoroscopic image of the stomach ST was described as an example in FIG. 11, but the fluoroscopic image of, the stomach ST is not limited to this. That is, the imaging target is arbitrary and for instance, may be blood veins or organs other than the stomach ST. Furthermore, the object that detects motion is the contrast agent CON in the example shown in FIG. 11, but the object of detecting motion is not limited to the contrast agent CON. That is, the object of detecting motion is arbitrary, and for instance, may be medical devices such as a catheter.

Next, as shown in FIG. 10, the X-ray diagnosis apparatus 1 determines whether to store the fluoroscopic image based on the image related information (Step S65). The process of determining whether to store the fluoroscopic image is realized by the fluoroscopic image storing control function 3013a in the processing circuitry 301. Specifically, the X-ray diagnosis apparatus 1 determines whether to store the fluoroscopic image in the memory based on the motion of the target detected at Step S63, which is the image analysis result analyzed at Step S63. More specifically, the X-ray diagnosis apparatus 1 determines whether the movement amount of the motion vector calculated at Step S63, i.e., the movement amount of the contrast agent CON within the region of interest ROI is greater than a specified amount of a preset movement amount, and determines whether to store the fluoroscopic image in the memory 303.

Then, at Step S65, if the movement amount of the contrast agent CON within the region of interest ROI is greater than the preset movement amount, i.e., when determining to store the fluoroscopic image in the memory 303 (Step S65: Yes), the X-ray diagnosis apparatus 1 stores the fluoroscopic image in the memory 303 (Step S25). On the other hand, at Step S65, if the movement amount of the contrast agent CON within the region of interest ROI is less than the preset movement amount, i.e., when determining not to store the fluoroscopic image in the memory 303 (Step S65: No), the X-ray diagnosis apparatus 1 determines whether to terminate the fluoroscopic imaging (Step S27).

Steps S25 to S31 after Step S65 is equivalent to that of FIG. 2 of the first embodiment described above, and description will be omitted. Then, the fluoroscopic image storing control process according to the second embodiment is terminated by executing Step S31.

As described above, in the X-ray diagnosis apparatus 1 according to the present embodiment, the X-ray diagnosis apparatus 1 acquires the fluoroscopic image as the image related information acquired within the certain period of time before or after the X-ray imaging, performs image analysis on the acquired fluoroscopic image, determines whether to store the fluoroscopic image captured before or after the X-ray imaging based on the image analysis result of the fluoroscopic image, and stores the fluoroscopic image captured before or after the X-ray imaging when determining to store in the memory 303 the fluoroscopic image captured before or after the X-ray imaging, fluoroscopic image may be stored in an appropriate and simple manner. That is, in the present embodiment, since the X-ray diagnosis apparatus 1 stores the fluoroscopic image in the memory 303 by detecting the movement amount of the object in the fluoroscopic image with the image analysis of the fluoroscopic image and if the movement amount of the movement is greater than a specific amount, the user may store necessary fluoroscopic image without additional operation.

Note that the fluoroscopic image captured before or after the X-ray imaging is stored in the memory 303 in the description of the second embodiment described above, but the X-ray diagnosis apparatus 1 may store in the memory either one of the fluoroscopic image captured before or after the X-ray imaging based on the image analysis result of the fluoroscopic image. That is, the X-ray diagnosis apparatus 1 may store at least one of the fluoroscopic image captured before or after the X-ray imaging based on the image analysis result of the fluoroscopic image. Likewise, in the second embodiment described above, the X-ray diagnosis apparatus 1 may select by the fluoroscopic image storing control function 3013 at least one of the fluoroscopic images captured before or after the X-ray imaging and store the selected fluoroscopic image in the memory 303.

Third Embodiment

In the X-ray diagnosis apparatus 1 according to the first embodiment described above, it was determined whether to store the fluoroscopic image in the memory 303 based on the operation content of the X-ray imaging switch 3071 which the user operates within the certain period of time before or after the X-ray imaging, which is the image related information, but embodiments are not limited to this. In a third embodiment, the captured image may be acquired as the image related information and it may be determined whether to store the fluoroscopic image in the memory 303 based on the image analysis result of the acquired captured image. Parts that differ from the first embodiment will be described below.

Figure 12:
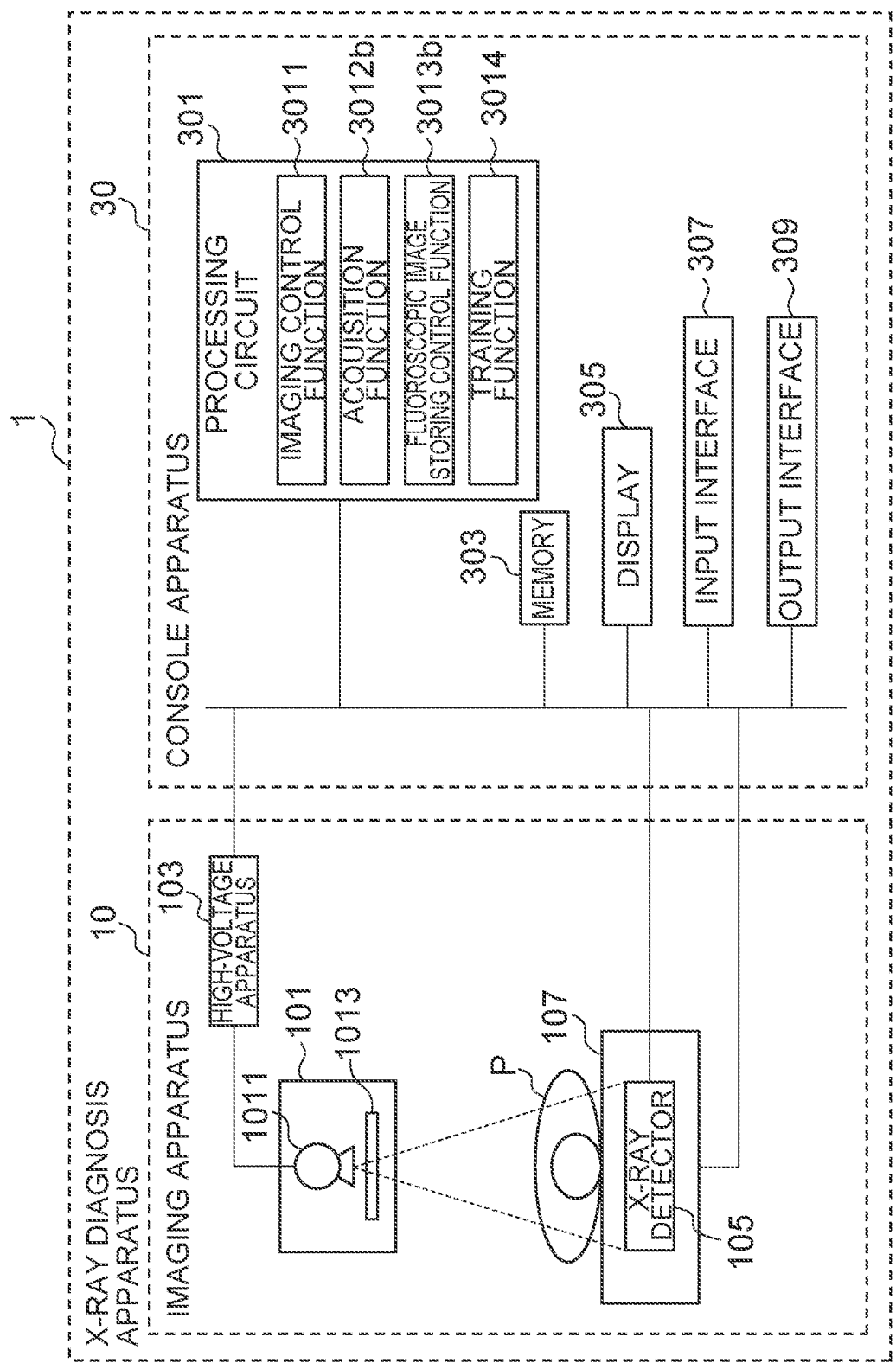
FIG. 12 is a block diagram that illustrates an exemplary configuration of the X-ray diagnosis apparatus according to a third embodiment.

FIG. 12 is a block diagram that illustrates a configuration example according to the third embodiment, which corresponds to FIG. 1 according to the first embodiment described above. As shown in FIG. 9, the X-ray diagnosis apparatus 1 according to the present embodiment is configured by adding a training function to the X-ray diagnosis apparatus 1 according to the first embodiment described above. Likewise, since the functions of the acquisition function and the fluoroscopic image storing control function are different from that of the first embodiment, those will be referred to as the acquisition function 3012b and the fluoroscopic image storing control function 3013b in the present embodiment. Note that the training function 3014 is equivalent to a training unit in the present embodiment. Likewise, configurations and functions other than the acquisition function 3012b, the fluoroscopic image storing control function 3013b, and the training function 3014 are equivalent to that of FIG. 1 in the first embodiment described above, description will be omitted.

The acquisition function 3012b is a function that acquired the image related information obtained within the certain period of time before or after the X-ray imaging. In the present embodiment, the acquisition function 3012b acquired the X-ray imaged captured image as the image related information.

The fluoroscopic image storing control function 3013b is a function that stores in the memory 303 at least one of the fluoroscopic images captured before and the X-ray imaging based on the image related information. In the present embodiment, the fluoroscopic image storing control function 3013b inputs the captured image acquired by the acquisition function 3012*b* to a trained model that went through machine learning to output fluoroscopic storing information related to storing at least one of the fluoroscopic image captured before and the X-ray imaging based on the captured image, and determines whether to store the fluoroscopic image in the memory 303 based on the fluoroscopic storing information related to storing at least one of the fluoroscopic image captured before and the X-ray imaging. That is, captured image is input, and the fluoroscopic image storing control function 3013*b* performs image analysis on the input captured image, inputs the captured image to the trained model that outputs fluoroscopic storing information based on the image analysis result of the fluoroscopic image, and determines whether to store the fluoroscopic image in the memory 303 based on the fluoroscopic storing information output from the trained model.

The fluoroscopic storing information is information related to storing the fluoroscopic image. The fluoroscopic storing information may include information related to a necessity of storing the fluoroscopic image in the memory 303, information related to the number of frames of the fluoroscopic image to store in the memory 303, and information related to selecting at least one of the fluoroscopic images captured before and the X-ray imaging. In the description below, an example is shown where the fluoroscopic storing information includes information related to the necessity of storing and the information related to the number of frames of the fluoroscopic image to store. Note that the fluoroscopic storing information may be configured including the information related to the necessity of storing or may include other information related to storing the fluoroscopic image.

Machine learning may use machine learning that uses a Support Vector Machine (SVM) or deep learning that uses a multilayer neural network such as a Convolutional Neural Network (CNN) or a Convolutional Deep Belief Neural Network. In the description below, an example is shown where the machine learning is the deep learning that uses the neural network and a machine learning model is a trained model that uses deep learning.

The training function 3014 is a function that builds a trained model. In the present embodiment, the training function 3014 builds the trained model, using a training data set with the plurality of captured images as a training data and a fluoroscopic storing result as a validation data. The fluoroscopic storing result (validation data) may be a data created by determining whether an expert requires the fluoroscopic image captured before or after the X-ray imaging when interpreting the captured image. The fluoroscopic storing result includes information related to whether the fluoroscopic image was stored and information related to the number of frames. Note that the fluoroscopic storing result (validation data) may be a data created by the training function 3014 determining whether the fluoroscopic image acquired before or after the X-ray imaging is necessary based on whether at least one of the fluoroscopic image, captured before or after the X-ray imaging of the captured image stored in the memory 303, is stored in the memory 303.

Figure 13:
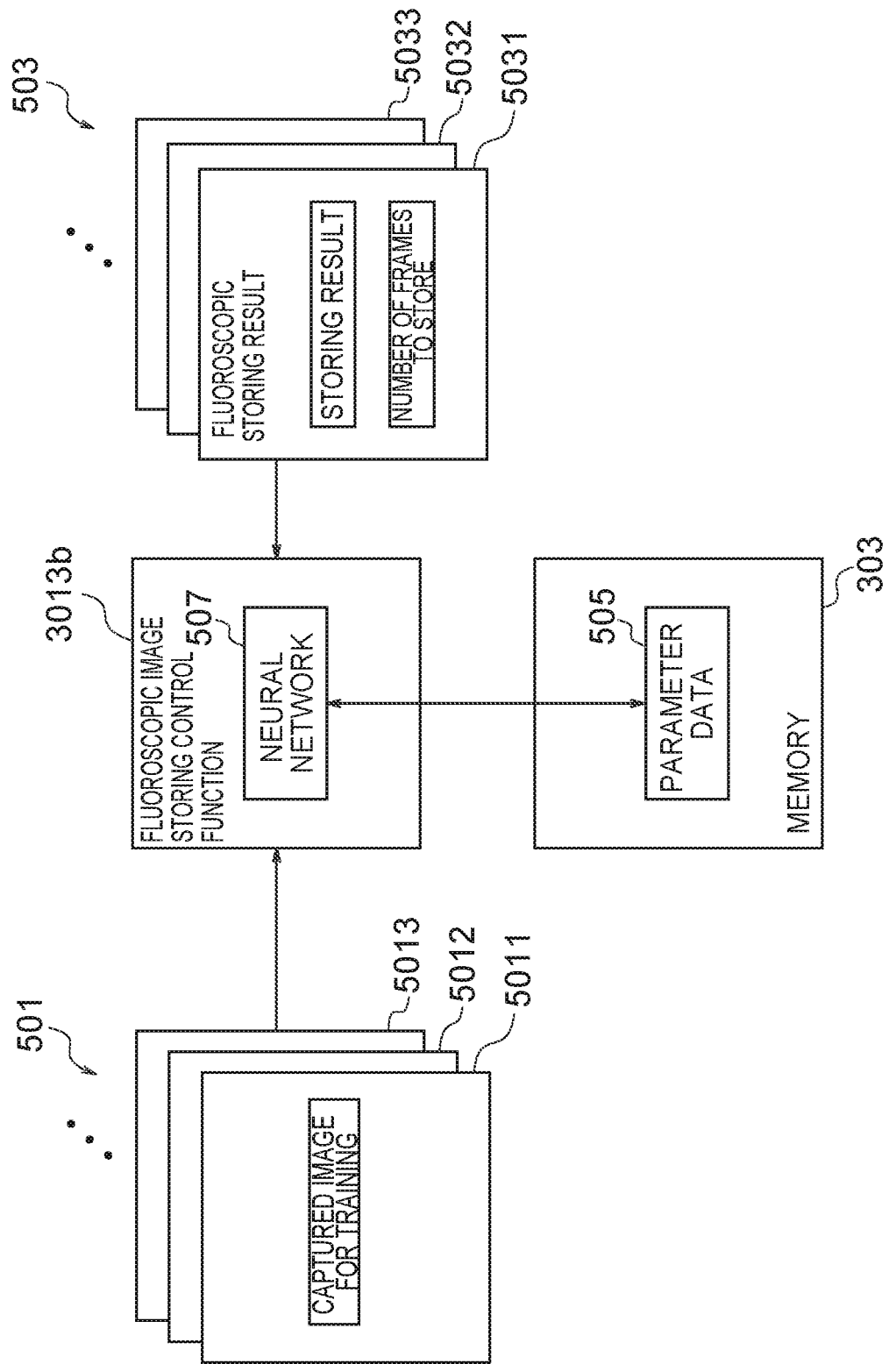
FIG. 13 is an exemplary diagram that describes an exemplary data flow during training the fluoroscopic image storing control process of the X-ray diagnosis apparatus according to the third embodiment.

FIG. 13 is an exemplary diagram that describes an exemplary data flow during training the fluoroscopic image storing control function 3013*b*. As shown in FIG. 13, during training, the fluoroscopic image storing control function 3013*b* sequentially updates a parameter data 505 stored in the memory 303 by performing deep learning using numerous training data set.

Each training data set of the numerous training data set consists of a training data group 501 and a validation data group 503. The training data group 501 is comprised by training data 5011, 5012, 5013 . . . , and each training data may consist of the captured image. Likewise, the validation data group 503 corresponding to each training data is comprised by fluoroscopic storing result 5031, 5032, 5033 . . . , and each fluoroscopic storing result 5031, 5032, 5033 . . . may consist of information related to the storing result or information related to the number of frames to store.

The fluoroscopic image storing control function 3013*b* is controlled by the training function 3014 and updates the parameter data 505 such that a result of processing the training data with the neural network 507 becomes closer to the verification data for every training data set that is given. That is, the fluoroscopic image storing control function 3013*b* is trained. In general, when a changing rate of the parameter data 505 converges within a threshold, it is determined that training is complete. Hereinafter, the parameter data 505 for which training is complete will be referred to as a trained parameter data 505*t*.

Figure 14:
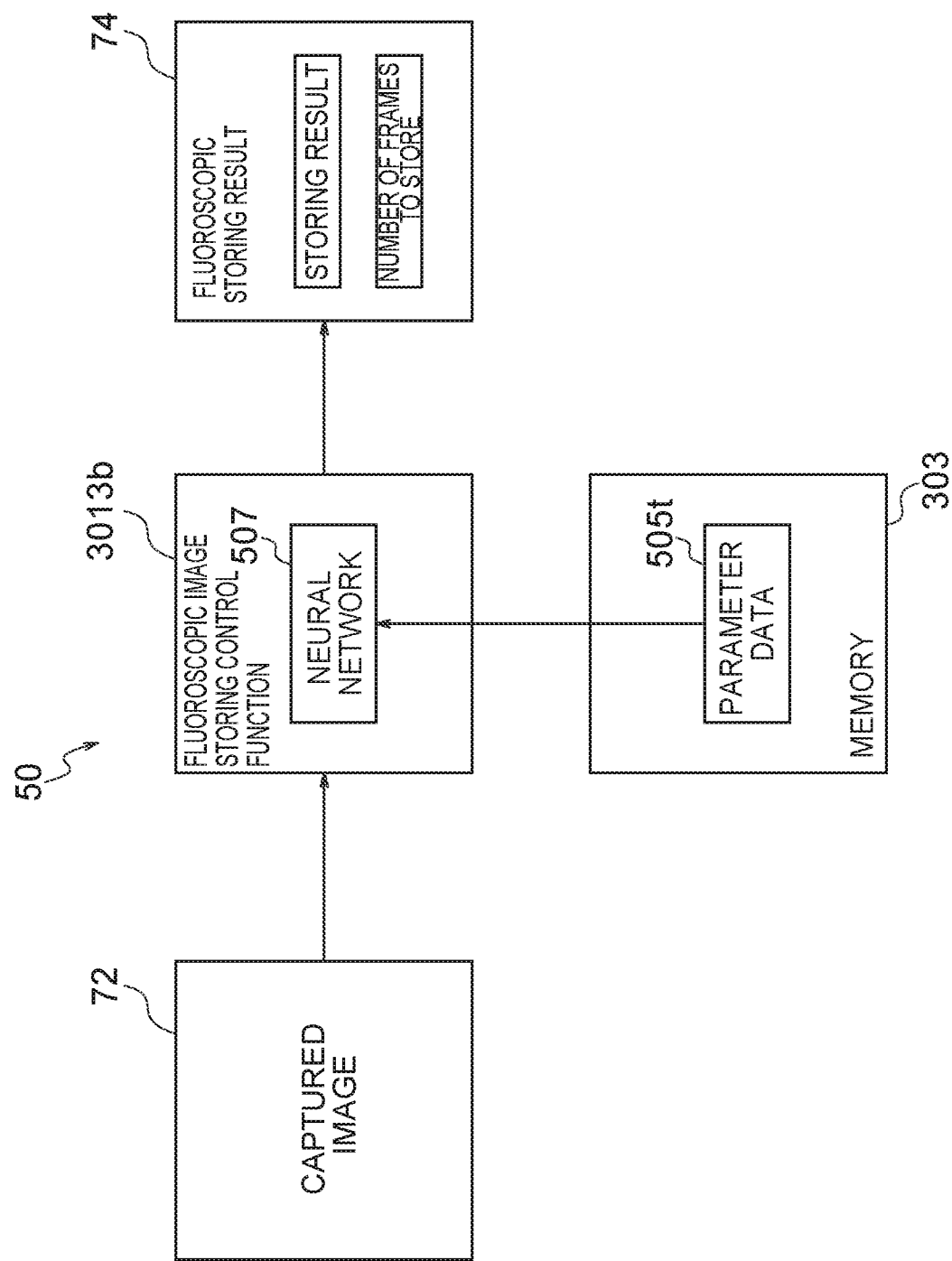
FIG. 14 is an exemplary diagram that describes an exemplary data flow during operating the fluoroscopic image storing control process of the X-ray diagnosis apparatus according to the third embodiment.

FIG. 14 is an exemplary diagram that describes an exemplary data flow during operating the fluoroscopic image storing control function 3013*b*. As shown in FIG. 14, during training, the fluoroscopic image storing control function 3013*b* inputs the captured image 72 acquired by the acquisition function 3012*b* into the trained model and determines whether to store at least one of the fluoroscopic images captured before or after the X-ray imaging based on the fluoroscopic storing information 74 output from the trained model.

Note that the trained parameter data 505*t* and the neural network 507 configures the trained model 50. Such method of training and building the trained model may use various methods. The neural network 507 is stored in the memory 303 in the form of the program. The trained parameter data 505*t* may be stored in the memory 303 or a storage connected with the processing circuitry 301. If the trained model 50 (neural network 507 and trained parameter data 505*t*) is stored in the memory 303, the fluoroscopic image storing control function 3013*b* that is executed by the processor of the processing circuitry 301 may input the captured image 72 in the trained model 50 by reading and executing the trained model 50 from the memory 303 and determined whether to store at least one of the fluoroscopic image captured before or after the X-ray imaging based on the fluoroscopic storing information 74 that is output from the trained model 50. The trained model 50 may also be built by integrated devices such as an Application Specific Integrated Circuit (ASIC) or a Field Programmable Gate Array (FPGA).

Figure 15:
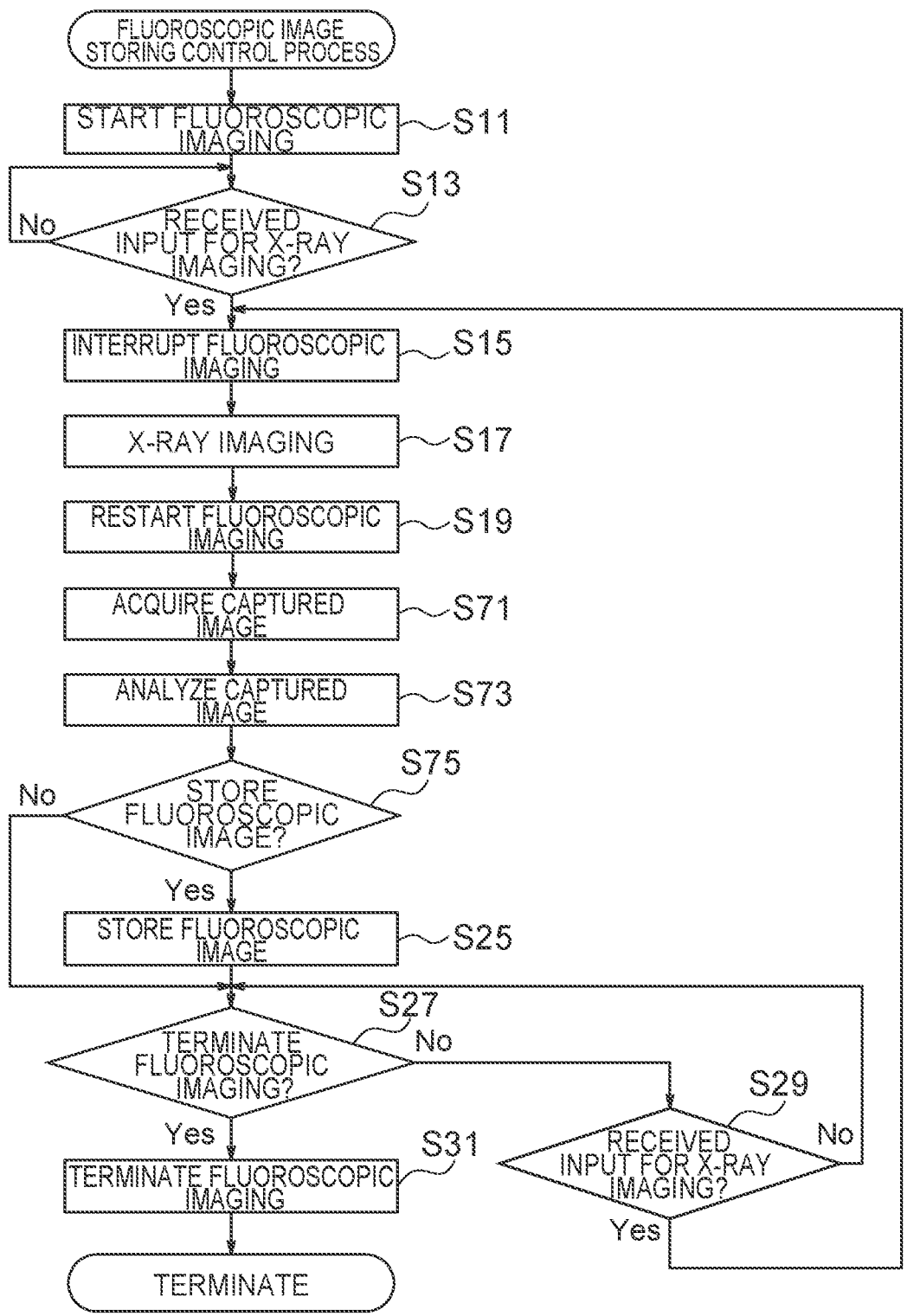
FIG. 15 is a flowchart that describes a content of the fluoroscopic image storing control process of the X-ray diagnosis apparatus according to the third embodiment.

Next, a fluoroscopic image storing control process executed in the X-ray diagnosis apparatus 1 according to the present embodiment will be described using FIG. 15. FIG. 15 is a flowchart that describes a content of the fluoroscopic image storing control process executed in the X-ray diagnosis apparatus 1 according to the present embodiment, which correspond to FIG. 2 of the first embodiment described above. In the fluoroscopic image storing control process shown in FIG. 15, the X-ray diagnosis apparatus 1 determines whether to store the fluoroscopic image in the memory 303 based on the image analysis result of the captured image 72. The fluoroscopic image storing control process may be a process executed when fluoroscopic imaging is started. Note that the process before Step S19 shown in FIG. 15 is equivalent to that of FIG. 2 of the first embodiment described above, and description will be omitted.

Next, as shown in FIG. 15, the X-ray diagnosis apparatus 1 acquired the captured image 72 as the image related information (Step S71). The process of acquiring the captured image 72 is realized by the acquisition function 3012 in the processing circuitry 301. Specifically, the X-ray diagnosis apparatus 1 acquired the captured image by the X-ray imaging at Step S17.

Next, as shown in FIG. 15, the X-ray diagnosis apparatus 1 image analyzes the captured image 72 (Step S73). The process of image analyzing the captured image 72 is realized by the fluoroscopic image storing control function 3013b in the processing circuitry 301. Specifically, the X-ray diagnosis apparatus 1 inputs the captured image 72 acquired at Step S71 to the trained model 50, image analyzes the inputted captured image 72, and outputs the fluoroscopic storing information based on the image analysis result of the captured image 72.

Next, as shown in FIG. 15, the X-ray diagnosis apparatus 1 determines whether to store the fluoroscopic image (Step S75). The process of determining whether to store the fluoroscopic image is realized by the fluoroscopic image storing control function 3013b in the processing circuitry 301. Specifically, the X-ray diagnosis apparatus 1 determines whether to store the fluoroscopic image based on the fluoroscopic storing information 74 that is output from the trained model 50 at Step S73.

Then, when determining to store the fluoroscopic image at Step S75 (Step S75: Yes), the X-ray diagnosis apparatus 1 stores the fluoroscopic image in the memory 303 (Step S25). On the other hand, when determining not to store the fluoroscopic image based on the fluoroscopic storing information 74 (Step S75: No), the X-ray diagnosis apparatus 1 determines whether to terminate the fluoroscopic imaging (Step S27).

Steps S25 to S31 after Step S75 is equivalent to that of FIG. 2 of the first embodiment described above, and description will be omitted. Then, the fluoroscopic image storing control process according to the third embodiment is terminated by executing Step S31.

As described above, in the present embodiment, since the X-ray diagnosis apparatus 1 acquires the captured image 72 as the image related information obtained within the certain period of time before or after the X-ray imaging, performs image analysis on the acquired captured image 72, determines whether to store the fluoroscopic image captured before or after the X-ray imaging in the memory 303 based on the image analysis result of the captured image 72, and stores the fluoroscopic image captured before or after the X-ray imaging in the memory 303 when determining to store the fluoroscopic image captured before or after the X-ray imaging in the memory 303, it is possible to store the fluoroscopic image in an appropriate an simple manner. That is, in the present embodiment, since it is made to input the captured image 72 to the trained model 50 that outputs fluoroscopic storing information related to storing the fluoroscopic image captured before or after the X-ray imaging based on the captured image 72 by image analyzing the captured image 72, and store the fluoroscopic image captured before or after the X-ray imaging in the memory 303 when determining that it is necessary to store the fluoroscopic image captured before or after the X-ray imaging based on the fluoroscopic storing information 74 that is output from the trained model 50, the user may train necessary fluoroscopic image without performing additional operation.

Note that the fluoroscopic image captured before or after the X-ray imaging was stored in the memory in the description of the third embodiment described above, but the X-ray diagnosis apparatus 1 may store either of the fluoroscopic image captured before or after the X-ray imaging based on the image analysis result of the fluoroscopic image. That is, the X-ray diagnosis apparatus 1 may store in the memory 303 at least one of the fluoroscopic images captured before or after the X-ray imaging based on the image analysis result of the captured image. In the third embodiment described above, the X-ray diagnosis apparatus 1 may also select by the fluoroscopic image storing control function 3013b at least one of the fluoroscopic image captured before the X-ray imaging and the fluoroscopic image captured after the X-ray imaging and store the selected fluoroscopic image in the memory 303.

[Third Modification]

In the first to third embodiments described above, when determining to store at least one of the fluoroscopic images captured before or after the X-ray imaging in the memory 303, the X-ray diagnosis apparatus 1 may also be modified to notify the user that the fluoroscopic image is stored in the memory 303. Parts that differ from the first embodiment will be described as a third modification where this modification is applied to the first embodiment.

Figure 16:
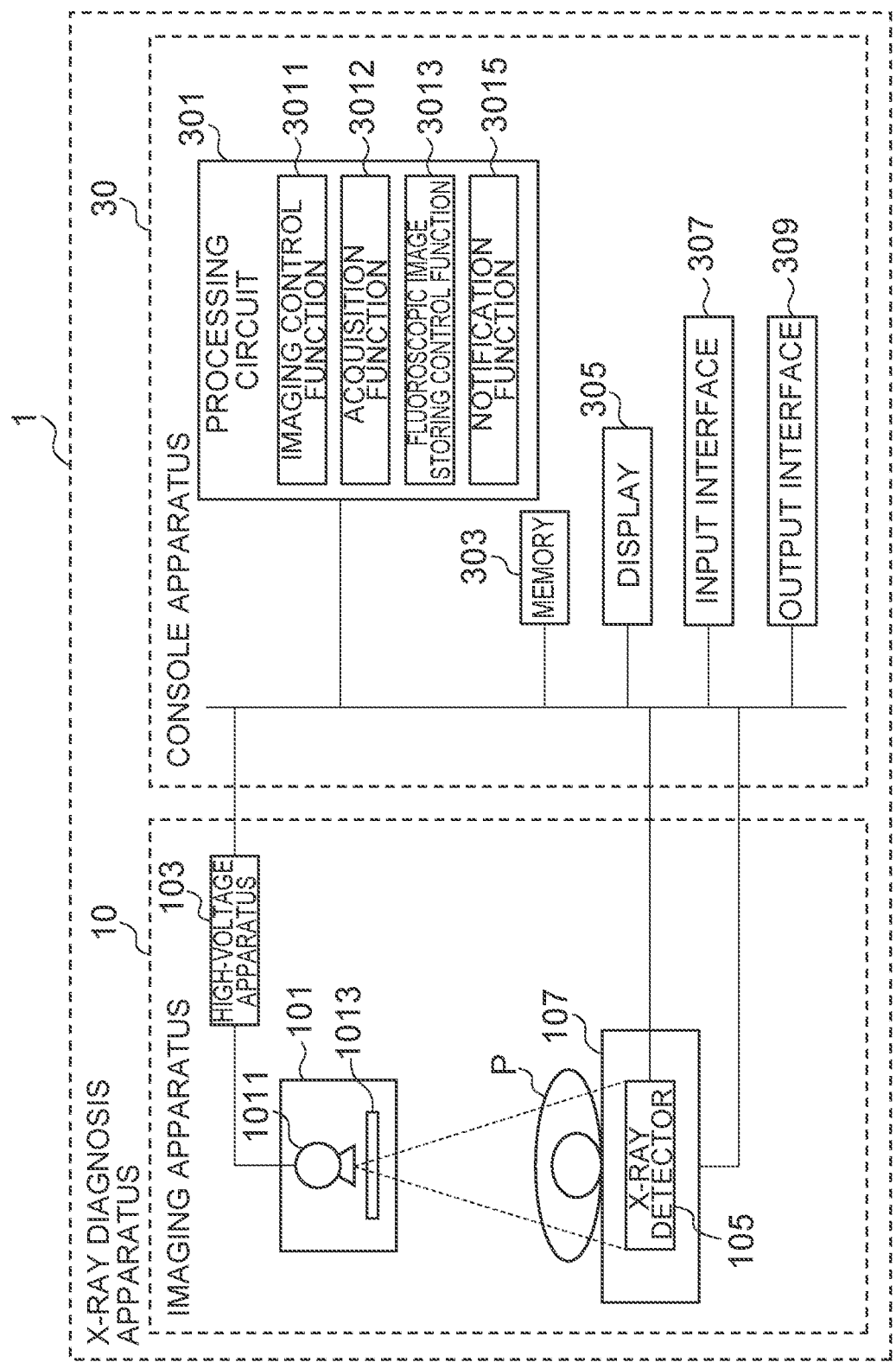
FIG. 16 is a block diagram that illustrates an exemplary configuration of the X-ray diagnosis apparatus according to a third modification.

FIG. 16 is a block diagram that illustrates an exemplary configuration of the X-ray diagnosis apparatus 1 according to the third modification, which corresponds to FIG. 1 of the first embodiment described above. As shown in FIG. 16, the X-ray diagnosis apparatus 1 according to the present modification is configured by adding a notification function 3015 to the processing circuitry 301 of the X-ray diagnosis apparatus 1 according to the first embodiment described above. Note that the notification function is equivalent to a notification unit in the present embodiment.

The notification function 3015 is a function that notifies the user that the fluoroscopic image is stored in the memory 303. The notification function 3015 may notify the user that the fluoroscopic image is stored in the memory 303 via a display 305.

Figure 17:
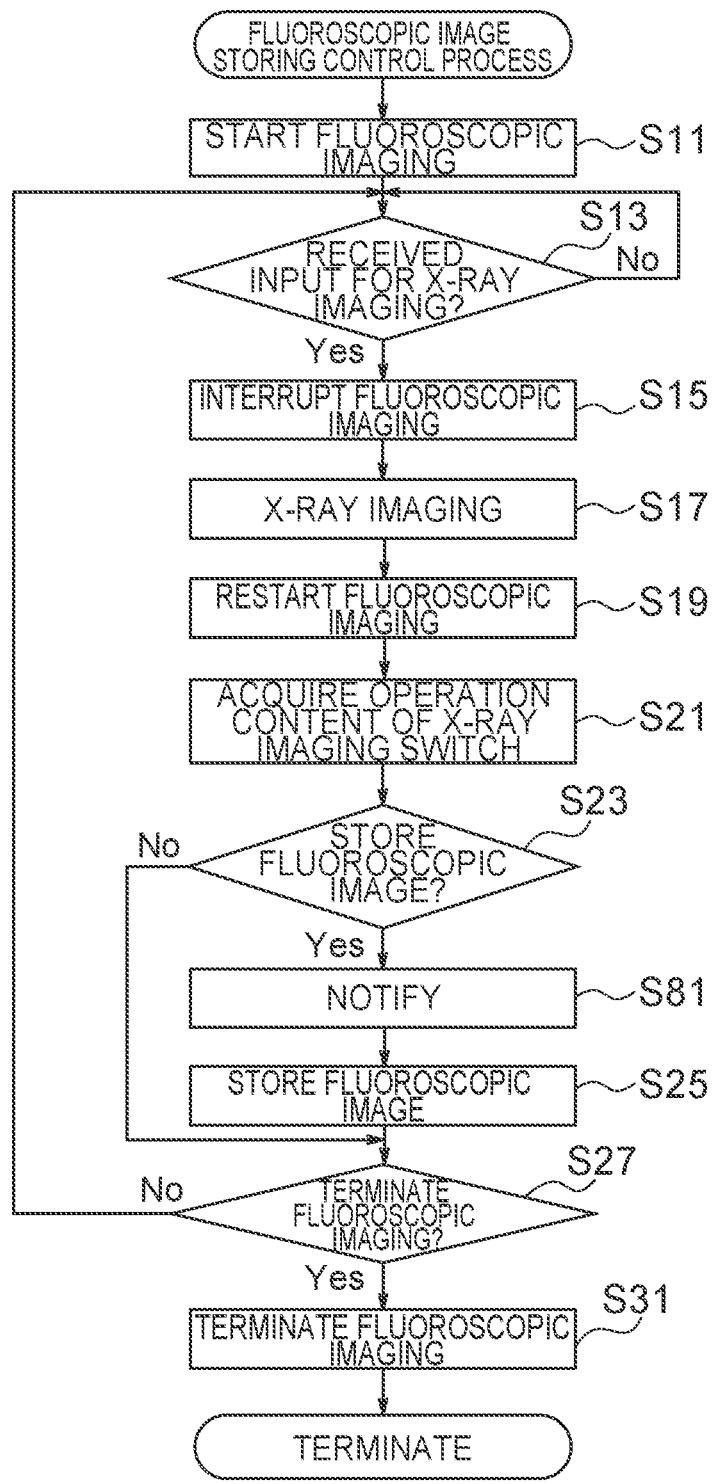
FIG. 17 is a flowchart that describes a content of the fluoroscopic image storing control process of the X-ray diagnosis apparatus according to the third modification.

FIG. 17 is a flowchart that describes a content of the fluoroscopic image storing control process executed in the X-ray diagnosis apparatus 1 according to the third modification. In the fluoroscopic image storing control process, the X-ray diagnosis apparatus 1 determines whether to store the fluoroscopic image based on the image related information, notifies the user when storing the fluoroscopic image, and stores the fluoroscopic image in the memory 303. For instance, the fluoroscopic image storing control process is a process executed when fluoroscopic imaging is started. Note that the process before Step S23 is equivalent to that of FIG. 1 described above, and description will be omitted.

Then, at Step S23 shown in FIG. 17, when time T is greater than the threshold, i.e., when determining to store the fluoroscopic image in the memory 303 (Step S23: Yes), the X-ray diagnosis apparatus 1 notifies the user that the fluoroscopic image is stored in the memory 303 (Step S81). The notification process is realized be the notification function 3015 in the processing circuitry 301. Specifically, the X-ray diagnosis apparatus 1 notifies the user that the fluoroscopic image is stored in the memory 303 via the display 305.

Figure 18:
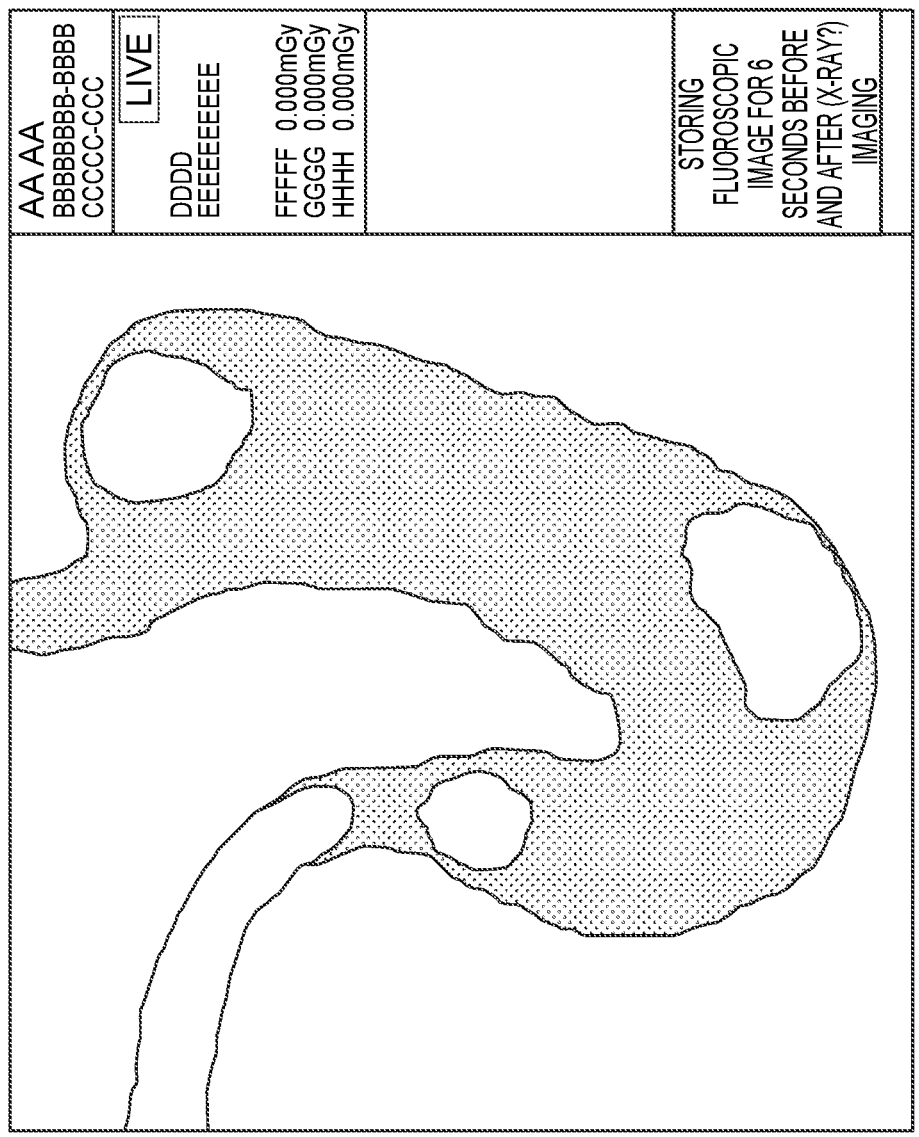
FIG. 18 is a diagram that illustrates an exemplary notification screen displayed on a display of the X-ray diagnosis apparatus according to the third modification.

FIG. 18 is a diagram that illustrates an exemplary notification screen displayed on the display 305 of the X-ray diagnosis apparatus 1 according to the present example. As shown in FIG. 18, the X-ray diagnosis apparatus 1 may display on the display 305 a message "Storing fluoroscopic image for 6 seconds before or after imaging" as the notification screen. By such, the user may confirm that the fluoroscopic image is stored in the memory 303.

Steps S27 to Step S31 after Step S81 is equivalent to that of FIG. 2 of the first embodiment described above, and description will be omitted. Then, the fluoroscopic image storing control process according to the third modification is terminated by executing Step S31.

As described above, the X-ray diagnosis apparatus 1 according to the present third modification may, when determining to store the fluoroscopic image in the memory 303, notify the user that the fluoroscopic image is stored in the memory via the display 305. For this reason, the X-ray diagnosis apparatus 1 may store the fluoroscopic image in an appropriate and simple manner, and the user may confirm that the fluoroscopic image is stored in the memory 303.

Note that, in third modification, an embodiment of notifying that the fluoroscopic image is stored in the memory 303 is not limited to displaying on the display 305. That is, the embodiment of notifying the user is arbitrary, and the X-ray diagnosis apparatus 1 may notify the user that the fluoroscopic image is stored in the memory 303 with voice via the output interface 309 or via vibration. As described, by the X-ray diagnosis apparatus 1 notifying the user that the fluoroscopic image is stored in the memory 303 via the output interface 309, the user may confirm that the fluoroscopic image is stored in the memory 303 without looking at the display 305.

The X-ray diagnosis apparatus 1 may also display on the display 305 a screen that sets the number of fluoroscopic images to store in the memory 303, such that the user may adjust the number of fluoroscopic images (number of frames) to store in the memory 303. The X-ray diagnosis apparatus 1 may also display on the display 305 a selection screen that selects the fluoroscopic image to store in the memory 303 such that the user may select to store in the memory at least one of the fluoroscopic images captured before or after the X-ray imaging. Furthermore, the description of the third modification described above was a description applied to the first embodiment, but it is clear that the present modification may be applied to the first and second modifications of the first embodiment, the second embodiment, and the third embodiment.

[Fourth Modification]

In the X-ray diagnosis apparatus 1 according to the first to third embodiments described above, when storing the fluoroscopic image in the memory 303 in the fluoroscopic image storing control process, the captured image 72 acquired by X-ray imaging and the fluoroscopic image captured by fluoroscopic imaging at least one of before or after the X-ray imaging may be associated and stored in the memory 303. By the X-ray diagnosis apparatus 1 associating and storing in the memory 303 the captured image acquired by X-ray imaging and the fluoroscopic image captured by fluoroscopic imaging at least one of before or after the X-ray imaging, when diagnosing using the captured image 72, and when the fluoroscopic image captured at least one of before or after the X-ray imaging that acquired the captured image 72 becomes a diagnosis material, the user may easily notice the fluoroscopic image associated with the captured image 72. Note that, it is clear that the description of the fourth modification described above may be applied not only to the first to third embodiments but also to the first and second modifications of the first embodiment.

[Fifth Modification]

Also, in the X-ray diagnosis apparatus 1 according to the first to third embodiments described above, when displaying the captured image 72 on the display 305, a button (referred to as a "button" hereinafter) that switches the display from the captured image 72 to the fluoroscopic image captured at least one of before or after the X-ray imaging and plays the fluoroscopic image may be displayed on the display 305. Parts that differ from the first embodiment will be described below as a fifth modification where the modification is applied to the first embodiment.

Figure 19:
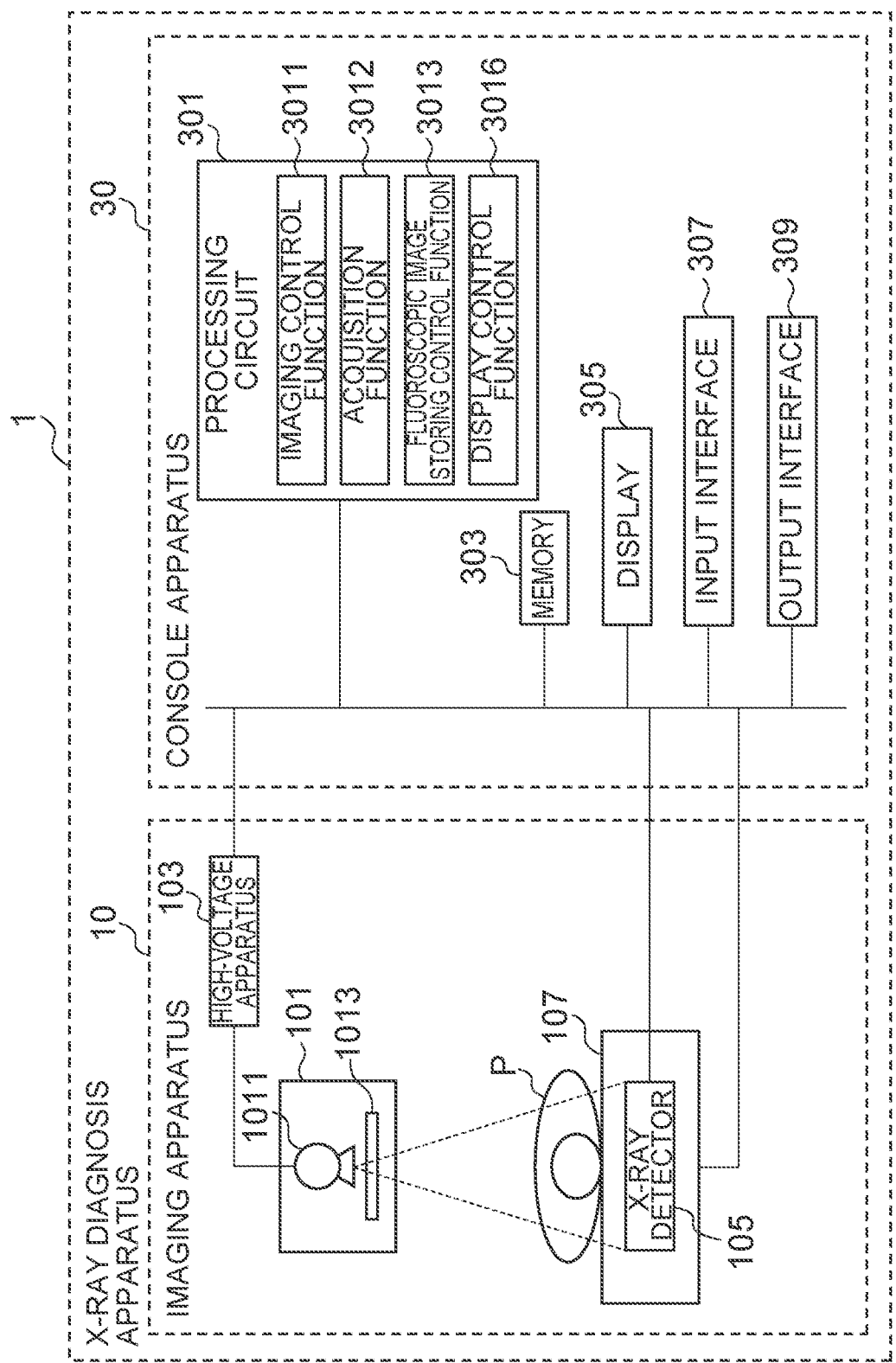
FIG. 19 is a block diagram that illustrates an exemplary configuration of the X-ray diagnosis apparatus according to a fifth modification.

FIG. 19 is a block diagram that illustrates an exemplary configuration of the X-ray diagnosis apparatus 1 according to the fifth modification, which corresponds to FIG. 1 in the first embodiment described above. As shown in FIG. 19, the X-ray diagnosis apparatus 1 according to the present modification is configured by adding a display control function 3016 to the processing circuitry 301 of the X-ray diagnosis apparatus 1 according to the first embodiment described above. Note that the display control function 3016 is equivalent to a display control unit of the present embodiment.

The display control function 3016 is a function that displays captured image 72 on the display 305. Also, in the present modification, the display control function 3016 displays the button on the display 305.

Figure 20:
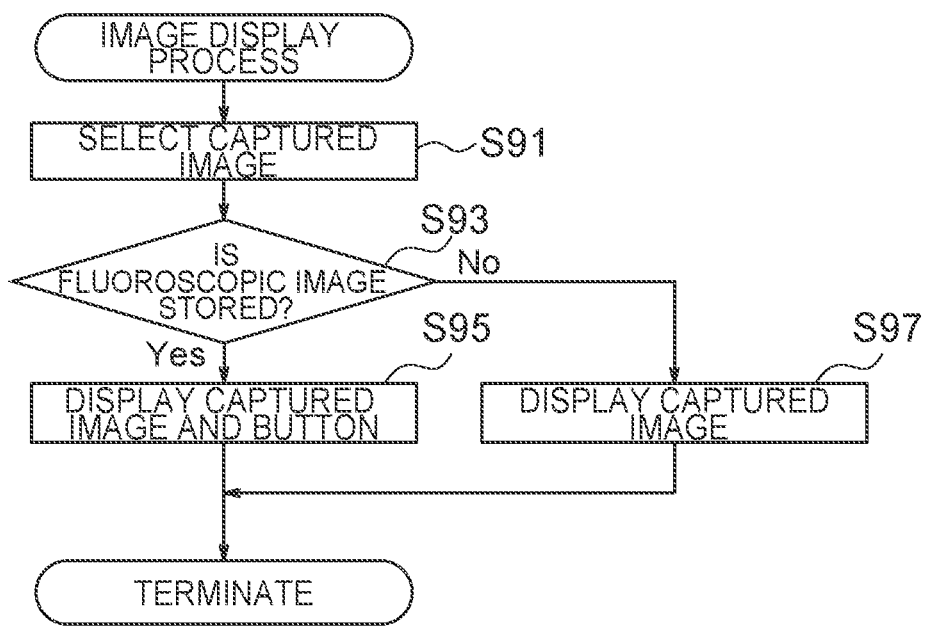
FIG. 20 is a flowchart that describes a content of the fluoroscopic image storing control process of the X-ray diagnosis apparatus according to the fifth modification.

FIG. 20 is a flowchart that describes a content of an image display process executed in the X-ray diagnosis apparatus 1 according to the fifth modification. In the image display process, the X-ray diagnosis apparatus 1 lets the user select the captured image 72 to display or displays the button on the display 305. The image display process may be a process executed when the user selects the captured image 72 to display on the display 305.

As shown in FIG. 20, the X-ray diagnosis apparatus 1 first allows to select the captured image 72 (Step S91). The process of allowing to select the captured image 72 is realized by the display control function 3016 in the processing circuitry 301. Specifically, the X-ray diagnosis apparatus 1 allows the user to select the captured image 72 to display on the display 305 via the input interface 307.

Next, as shown in FIG. 20, the X-ray diagnosis apparatus 1 determines whether the fluoroscopic image is stored (Step S93). The process of determining whether the fluoroscopic image is stored is realized by the display control function 3016 in the processing circuitry 301. Specifically, the X-ray diagnosis apparatus 1 determines whether the fluoroscopic image captured at least one of before or after the X-ray imaging for the captured image 72 selected at Step S91.

Then, if the fluoroscopic image is stored at Step S93 (Step S93: Yes), the X-ray diagnosis apparatus 1 displays the captured image 72 and the button (Step S95). The process of displaying the captured image 72 and the button is realized by the display control function 3016 in the processing circuitry 301. Specifically, the X-ray diagnosis apparatus 1 displays the captured image selected at Step S91 and the button on the display 305.

Figure 21:
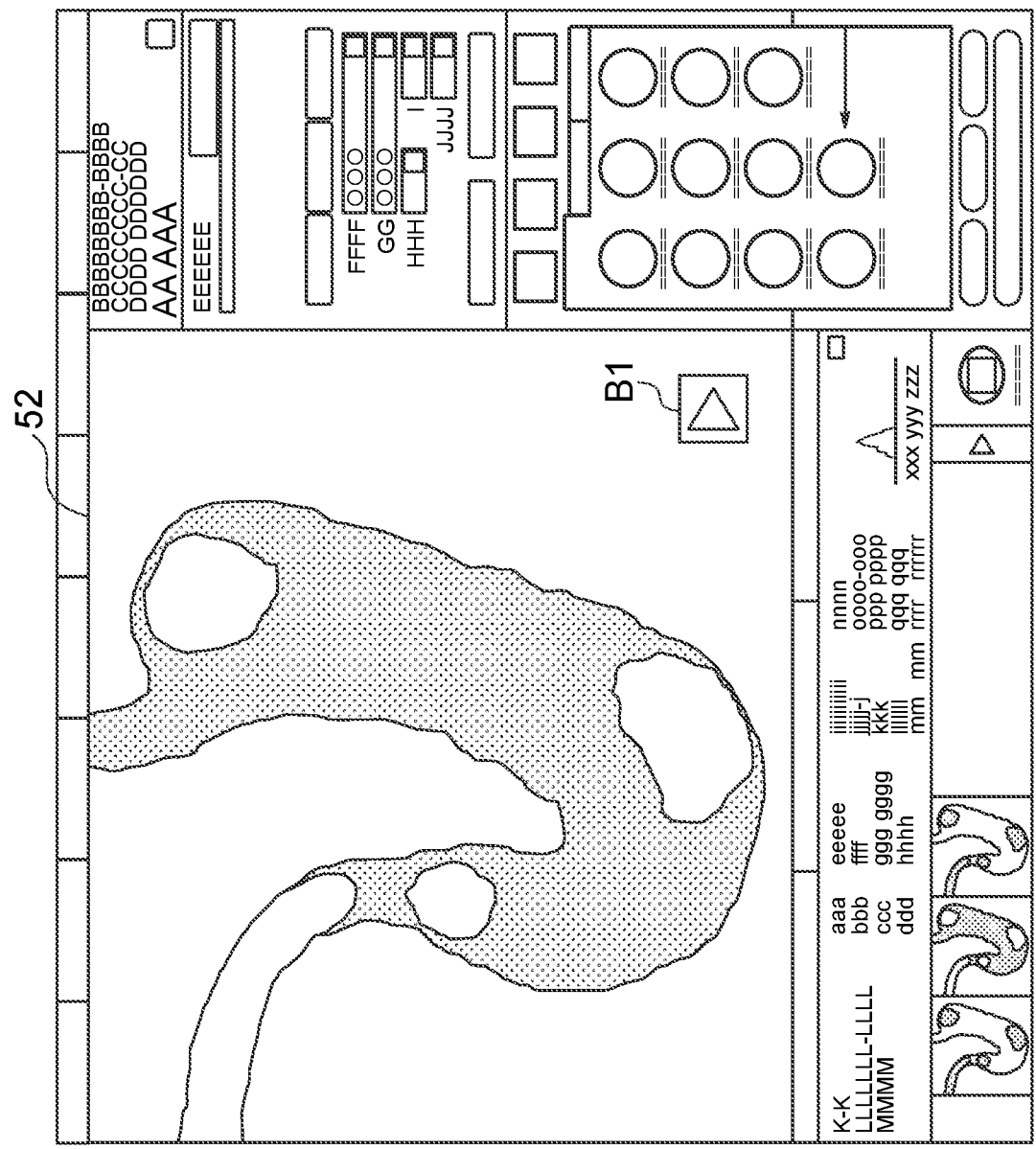
FIG. 21 is a diagram that illustrates an exemplary captured image and a button displayed on the display of the X-ray diagnosis apparatus according to the fifth modification.

FIG. 21 is a diagram that illustrates an exemplary captured image 72 and the button displayed on the display 305 of the X-ray diagnosis apparatus 1 according to the present modification. As shown in FIG. 21, the captured image 72 is displayed on the display 305 and the button B1 is displayed on the captured image 72.

On the other hand, if the fluoroscopic image is not stored at Step S93 (Step S93: No), the X-ray diagnosis apparatus 1 displays the captured image 72 (Step S97). The process of displaying the captured image 72 is realized by the display control function 3016 in the processing circuitry 301. Specifically, the X-ray diagnosis apparatus 1 displays the captured image 72 selected at Step S91 on the display 305 without displaying the button B1.

The image control process according to the present embodiment is terminated by executing either of Steps S95 or S97.

As described above, in the X-ray diagnosis apparatus 1 according to the present modification, since the captured image 72 is selected by the user, and if the fluoroscopic image captured at least one of before or after the X-ray imaging for the captured image 72 is stored in the memory 303, the captured image 72 is displayed with the button B1 on the display 305, switches the display from the captured image 72 to the fluoroscopic image captured at least one of before or after the X-ray imaging by the user selecting the button B1, and made possible to play the fluoroscopic image, the user may easily switch from the captured image 72 to the fluoroscopic image, and user convenience is improved.

Note that, in the fifth modification described above, the captured image 72 and the fluoroscopic image may be displayed on the display 305 at the same time. Likewise, when displaying the captured image 72 and the fluoroscopic image at the same time, the button B1 to switch between the captured image 72 and the fluoroscopic image may not be displayed. Likewise, when displaying the captured image 72 and the fluoroscopic image at the same time, the fluoroscopic image may be automatically played when displaying the fluoroscopic image. Furthermore, the description of the fifth modification described above was a description applied to the first embodiment, but it is clear that the present embodiment may be applied to the first and second modifications of the first embodiment, second and third embodiments, and the third and fourth modifications.

[Sixth Modification]

In the X-ray diagnosis apparatus 1 according to the first to third embodiments described above, when playing the fluoroscopic image on the display 305, it is also possible to insert an interpolated image generated based on at least one of the captured image 72, the fluoroscopic image, and a black image, and play the fluoroscopic image on the display 305 so as to maintain the framerate of the fluoroscopic image. Parts that differ from that of the first embodiment will be described as a sixth modification where the modification is applied to the first embodiment.

Figure 22:
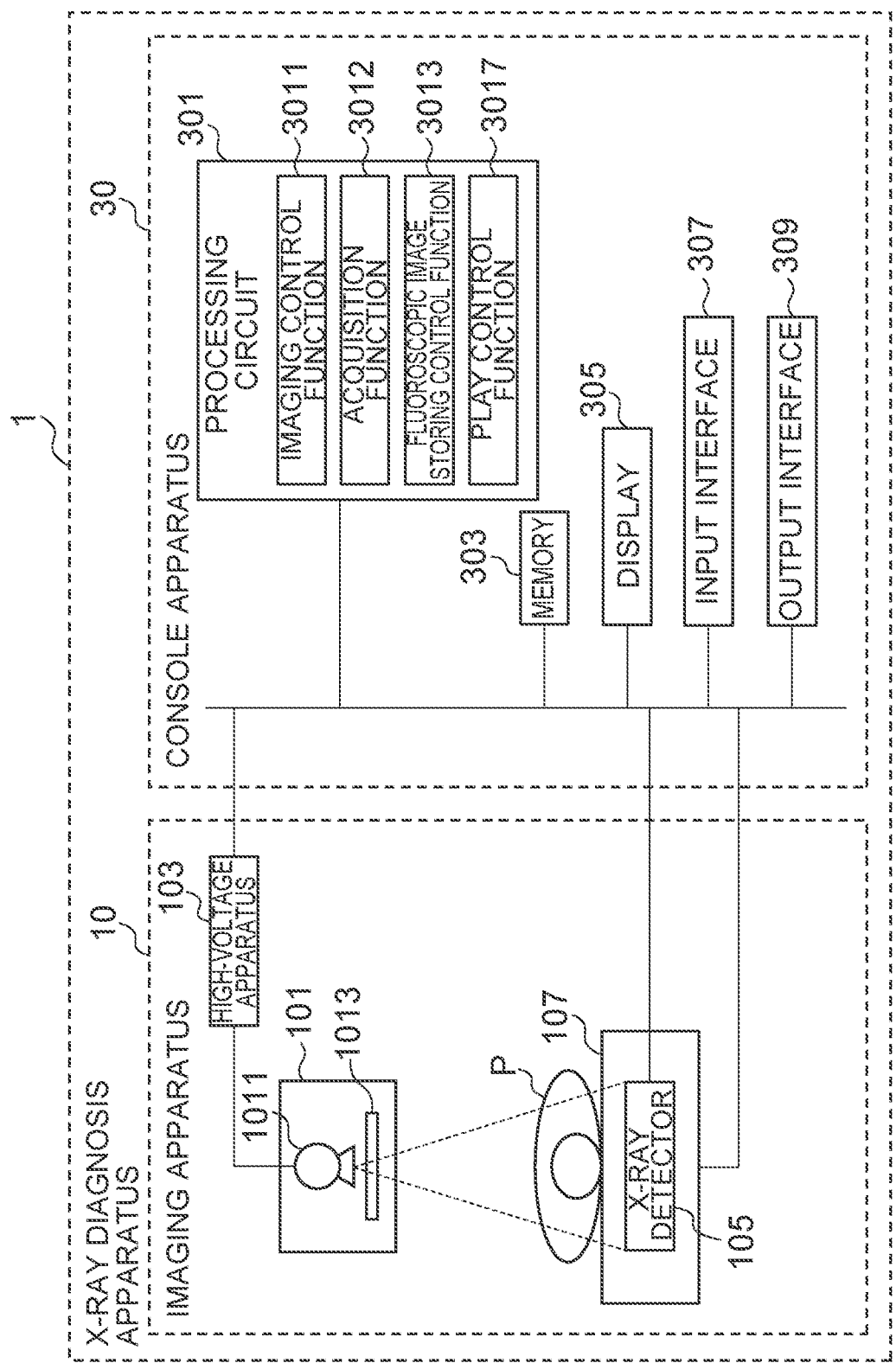
FIG. 22 is a block diagram that illustrates the X-ray diagnosis apparatus according to a sixth modification.

FIG. 22 is a block diagram that illustrates an exemplary configuration of the X-ray diagnosis apparatus 1 according to the sixth modification, which corresponds to FIG. 1 according to the first embodiment described above. As shown in FIG. 22, the X-ray diagnosis apparatus 1 according to the present modification is configured by adding a play control function 3017 to the processing circuitry 301 of the X-ray diagnosis apparatus 1 according to the first embodiment described above. Note that the play control function 3017 is equivalent to a play control unit according to the present embodiment.

The play control function 3017 is a function that plays the fluoroscopic image on the display 305. Also in the present embodiment, the play control function 3017 inserts the interpolated image generated based on at least one of the captured image 72, the fluoroscopic image, and a black image, and plays the fluoroscopic image on the display 305 so as to maintain the framerate of the fluoroscopic image.

Figure 23:
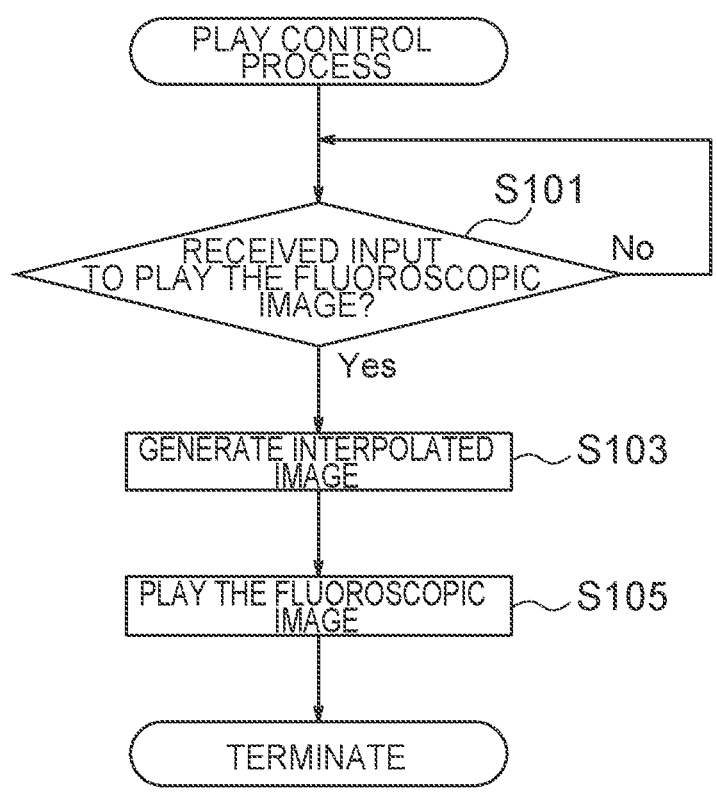
FIG. 23 is a flowchart that describes a content of the play control process of the X-ray diagnosis apparatus according to the sixth modification.

Next, a play control process that plays the fluoroscopic image executed in the X-ray diagnosis apparatus 1 according to the present modification will be described using FIGS. 23 and 24. FIG. 23 is a flowchart that describes a content of the play control process executed in the X-ray diagnosis apparatus 1 according to the present modification. FIG. 24 is a timing chart that describes a timing of inserting the interpolated image into the fluoroscopic image. In the play control process shown in FIG. 23, the X-ray diagnosis apparatus 1 is a process executed when receiving an input to play the fluoroscopic image.

As shown in FIG. 23, the X-ray diagnosis apparatus 1 first determines whether the input to play the fluoroscopic image was received (Step S101). The process of determining whether the input to play the fluoroscopic image is realized by the play control function 3017 in the processing circuitry 301. Specifically, the X-ray diagnosis apparatus 1 determines whether the input to play the fluoroscopic image was received from the user via the input interface 307. Then, if the input to play the fluoroscopic image was not received from the user via the input interface 307 (Step S101: No), the X-ray diagnosis apparatus 1 repeats Step S101 and standbys.

On the other hand, when the input to play the fluoroscopic image was received from the user (Step S101: Yes), the X-ray diagnosis apparatus 1 generates the interpolated image (Step S103) as shown in FIG. 23. The process of generating the interpolated image is realized by the play control function 3017 in the processing circuitry 301. Specifically, the X-ray diagnosis apparatus 1 generates the interpolated image to insert into the fluoroscopic image that received the input to play at Step S101, so as to maintain the framerate of the fluoroscopic image captured before or after the X-ray imaging.

More specifically, as shown in FIG. 24, when X-ray imaging is performed during fluoroscopic imaging, there is a time when fluoroscopic image cannot be acquired because the X-ray diagnosis apparatus 1 switches from fluoroscopic imaging to X-ray imaging. Since the captured image 72 is acquired during the time when the fluoroscopic image cannot be acquired, the interpolated image is generated by matching the image quality of the captured image 72, acquired during the time when the fluoroscopic image cannot be acquired, to the image quality of the fluoroscopic image. Note that, the pulse fluoroscopic imaging which performs fluoroscopic imaging by discontinuously irradiating X-ray in the fluoroscopic image shown in FIG. 24, but the fluoroscopic imaging shown in FIG. 24 may be the continuous fluoroscopic imaging that performs fluoroscopic imaging by continuously irradiating X-ray.

Next, as shown in FIG. 23, the X-ray diagnosis apparatus 1 plays the fluoroscopic image (Step S105). The step of playing the fluoroscopic image is realized by the play control function 3017 in the processing circuitry 301. Specifically, as shown in FIG. 24, the X-ray diagnosis apparatus 1 plays the fluoroscopic image by inserting the interpolated image generated at Step S103 to the fluoroscopic image that received the input to play at Step S101 and displaying on the display 305. The play control process according to the present example is terminated by executing Step S105.

As described above, since the X-ray diagnosis apparatus 1 according to the present modification performs X-ray imaging between fluoroscopic imaging, and even when there exists the time when fluoroscopic image is not acquired, plays the fluoroscopic image on the display 305 by inserting the interpolated image generated based on the captured image 72, the user may confirm playing the fluoroscopic image which the framerate of the fluoroscopic image is maintained and diagnose.

Note that, if the interpolated image is displayed during playing the fluoroscopic image, the X-ray diagnosis apparatus 1 may display on the display 305 that this is the interpolated image. Likewise, the generated interpolated image is not limited to use the captured image 72. For instance, the X-ray diagnosis apparatus 1 may generate the interpolated image based on the fluoroscopic image captured by fluoroscopic imaging right before the X-ray imaging. That is, when playing the fluoroscopic image, the X-ray diagnosis apparatus 1 may display the fluoroscopic image captured by the fluoroscopic imaging right before the X-ray imaging for a portion where the fluoroscopic image was not obtained. Also, for instance, the X-ray diagnosis apparatus 1 may generate black image as the interpolated image, insert the black image to the fluoroscopic image, and play the fluoroscopic image. Furthermore, if the framerate cannot be maintained by the single interpolated image, the X-ray diagnosis apparatus 1 may generate a plurality of interpolated images, insert the generated plurality of interpolated images to the fluoroscopic image, and play the fluoroscopic image.

As described above, in the present embodiment, the processing circuit 18, for instance, is configured by the processor. Note that the word "processor" used in above descriptions means circuits such as, for example, a Central Processing Unit (CPU), a Graphics Processing Unit (GPU), an Application Specific Integrated Circuit (ASIC), a programmable logic device (for example, a Simple Programmable Logic Apparatus (SPLD), a Complex Programmable Logic Apparatus (CPLD), and a Field Programmable Gate Array (FPGA)). The processor executes functions by reading and executing programs stored in the memory. Note that programs may be configured to be directly integrated in the processor instead of being storing in the memory. In this case, the processor realizes functions by reading and executing programs stored in the circuit. Note that the processor is not limited to be arranged as a single processor circuit, but may be configured as a single processor by combining a plurality of independent circuits to realize functions. Furthermore, a plurality of component elements in FIG. 1 may be integrated into one processor to realize the functions.

While certain embodiments have been described, these embodiments have been presented by way of example only and are not intended to limit the scope of the inventions. The embodiments may be in a variety of other forms. Furthermore, various omissions, substitutions and changes may be made without departing from the spirit of the inventions. The embodiments and their modifications are included in the scope and the subject matter of the invention, and at the same time included in the scope of the claimed inventions and their equivalents.

The invention claimed is:

1. An X-ray diagnosis apparatus, comprising:
an imager configured to perform imaging by irradiating an X-ray to a subject to acquire a captured image by X-ray imaging and acquire a fluoroscopic image by fluoroscope imaging;
an input interface configured to receive a user operation, the input interface including an X-ray imaging switch and a fluoroscopic imaging switch, the X-ray imaging switch being a switch to control whether to perform the X-ray imaging, and the fluoroscopic imaging switch being a switch to control whether to perform fluoroscopic imaging; and
processing circuitry configured to
acquire an operation content of the X-ray imaging switch as imaging related information obtained within a certain period of time before or after the X-ray imaging,
determine whether to store the fluoroscopic image based on the acquired operation content of the X-ray imaging switch; and
store, in a memory, the fluoroscopic image, which is captured one of before or after the X-ray imaging, based on the imaging related information.

2. The X-ray diagnosis apparatus of claim 1, wherein the processing circuitry is further configured to determine a number of frames of the fluoroscopic image stored in the memory, in response to an operation time of the input interface.

3. The X-ray diagnosis apparatus of claim 1, wherein the processing circuitry is further configured to store, within the memory, to the captured image imaged by the X-ray imaging in association with the fluoroscopic image imaged by the fluoroscopic imaging related to at least one of the X-ray imaging before or after.

4. The X-ray diagnosis apparatus of claim 1, wherein the processing circuitry is further configured to select at least one of fluoroscopic images captured before the X-ray imaging and after the X-ray imaging, and store the selected at least one of the fluoroscopic images in the memory.

5. The X-ray diagnosis apparatus of claim 1, wherein the processing circuitry is further configured to notify that the fluoroscopic image is stored in the memory.

6. The X-ray diagnosis apparatus of claim 1, wherein the processing circuitry is further configured cause a display to display a button to play the fluoroscopic image by switching the display from the captured image to the fluoroscopic image, which is captured at least one of before or after the X-ray imaging, when displaying the captured image.

7. The X-ray diagnosis apparatus of claim 1, wherein the processing circuitry, while playing the fluoroscopic image, is further configured to insert an interpolated image in the fluoroscopic image, and cause the display to play the fluoroscopic image so as to maintain a framerate of the fluoroscopic image captured before or after the X-ray imaging,
the interpolated image being an image generated based on at least one of the captured image, the fluoroscopic image captured at least one of before or after the X-ray imaging, and a black image.

8. The X-ray diagnosis apparatus of claim 7, wherein the processing circuitry is further configured to insert the interpolated image in the fluoroscopic image and play the fluoroscopic image on the display, the interpolated image being an image generated by changing an image quality of one of the captured image and the fluoroscopic image captured at least one of before or after the X-ray imaging so as to match to an image quality.

9. The X-ray diagnosis apparatus of claim 7, wherein the processing circuitry, when causing the display to display the interpolated image, is further configured to cause the display to display information indicating that the fluoroscopic image is the interpolated image.

10. The X-ray diagnosis apparatus of claim 1, wherein the processing circuitry is further configured to acquire one X-ray image as the captured image by a discrete X-ray irradiation in the X-ray imaging, and acquire the X-ray image that is continuous in time as the fluoroscopic image by a continuous or discontinuous X-ray irradiation in the fluoroscopic imaging.

11. The X-ray diagnosis apparatus of claim 1, wherein the processing circuitry is further configured to:
when the X-ray imaging is performed during the fluoroscopic imaging, acquire an operation content of the X-ray imaging switch as the imaging related information, and determine whether to store the fluoroscopic image based on the operation content of the X-ray imaging switch.

12. The X-ray diagnosis apparatus of claim 1, wherein the X-ray imaging switch is a hand switch, and the fluoroscopic imaging switch is a foot switch.

13. A control method of an X-ray diagnosis apparatus that comprises an input interface configured to receive a user operation, the input interface including an X-ray imaging switch and a fluoroscopic imaging switch, the X-ray imaging switch being a switch to control whether to perform the X-ray imaging, and the fluoroscopic imaging switch being a switch to control whether to perform fluoroscopic imaging, the control method comprising:
- performing X-ray imaging and fluoroscopic imaging by irradiating X-ray to a subject;
- acquiring an operation content of the X-ray imaging switch as imaging related information obtained within a certain period of time before or after the X-ray imaging;
- determining whether to store the fluoroscopic image based on the acquired operation content of the X-ray imaging switch; and
- storing, in a memory, a fluoroscopic image captured by the fluoroscopic image captured at least one of before or after the X-ray imaging based on the imaging related information.

* * * * *